(12) United States Patent
Yano et al.

(10) Patent No.: US 7,583,382 B2
(45) Date of Patent: Sep. 1, 2009

(54) OPTICAL MEASUREMENT APPARATUS

(75) Inventors: Takakazu Yano, Tokyo (JP); Kenji Matsumoto, Tokyo (JP); Tadahiro Fukuda, Tokyo (JP); Miharu Sugiura, Tokorozawa (JP)

(73) Assignee: Citizen Holdings Co., Ltd., Tokyo (JP)

( * ) Notice: Subject to any disclaimer, the term of this patent is extended or adjusted under 35 U.S.C. 154(b) by 0 days.

(21) Appl. No.: 10/594,528

(22) PCT Filed: Mar. 29, 2005

(86) PCT No.: PCT/JP2005/006564

§ 371 (c)(1),
(2), (4) Date: Jul. 30, 2007

(87) PCT Pub. No.: WO2005/093410

PCT Pub. Date: Oct. 6, 2005

(65) Prior Publication Data
US 2007/0273868 A1   Nov. 29, 2007

(30) Foreign Application Priority Data
Mar. 29, 2004 (JP) ............................. 2004-094194
Sep. 24, 2004 (JP) ............................. 2004-276282
Sep. 27, 2004 (JP) ............................. 2004-278936

(51) Int. Cl.
*G01N 21/00* (2006.01)
*G01N 3/00* (2006.01)
*C02F 1/461* (2006.01)

(52) U.S. Cl. ..................... 356/436; 356/432; 356/72; 356/36; 205/742; 205/749; 210/745

(58) Field of Classification Search ......... 356/432–444, 356/36–41, 72, 317, 318; 250/565, 573–574; 205/742, 746, 749, 775; 210/748, 205, 282, 210/287; 436/73, 79–84, 177
See application file for complete search history.

(56) References Cited

U.S. PATENT DOCUMENTS

| | | | | |
|---|---|---|---|---|
| 4,908,676 A | * | 3/1990 | Bedell et al. | 356/72 |
| 5,624,544 A | * | 4/1997 | Deguchi et al. | 205/742 |
| 6,086,748 A | * | 7/2000 | Durst et al. | 205/775 |
| 6,294,073 B1 | * | 9/2001 | Shirota et al. | 205/749 |
| 6,414,182 B1 | * | 7/2002 | Shingai et al. | 560/209 |
| 6,682,934 B2 | * | 1/2004 | Jolly et al. | 436/73 |
| 6,835,295 B1 | * | 12/2004 | Jangbarwala | 205/349 |

(Continued)

FOREIGN PATENT DOCUMENTS

JP         57-127848         8/1982

(Continued)

*Primary Examiner*—Sang Nguyen
(74) *Attorney, Agent, or Firm*—Finnegan, Henderson, Farabow, Garrett & Dunner, L.L.P.

(57) ABSTRACT

An object of the present invention is to provide an optical measurement apparatus equipped with an ion-exchange resin for pretreating a sample, thereby enabling the concentration of component in the sample to be measured with higher accuracy. The optical measurement apparatus of the present invention includes, in addition to the ion-exchange resin, an optical measurement section for measuring, based on the optical characteristics of the component, the concentration of the component in the sample after the sample is passed through the ion-exchange resin.

16 Claims, 19 Drawing Sheets

U.S. PATENT DOCUMENTS

| | | | |
|---|---|---|---|
| 7,261,816 B2 * | 8/2007 | Suzuki et al. | 210/282 |
| 2003/0206846 A1 * | 11/2003 | Jangbarwala | 423/241 |
| 2004/0256329 A1 * | 12/2004 | Meserol et al. | 210/748 |

FOREIGN PATENT DOCUMENTS

| | | |
|---|---|---|
| JP | 8-62220 | 3/1996 |
| JP | 9-80037 | 3/1997 |
| JP | 2001-141709 | 5/2001 |
| JP | 2002-98628 | 4/2002 |

* cited by examiner

OPTICAL MEASUREMENT APPARATUS

FIELD OF THE INVENTION

The present invention relates to an optical measurement apparatus for measuring the concentration of an optically active substance and, more particularly, to an optical measurement apparatus that can highly accurately measure the concentration of an optically active substance in a sample pretreated with an ion-exchange resin.

BACKGROUND OF THE INVENTION

In the prior art, it is known to provide, as a means for measuring the concentration of an optically active substance in a sample, a method that obtains the concentration from the optical rotation that a beam of light experiences when it is passed through the sample. On the other hand, enzyme-based methods such as the GOP method are known, for example, for measuring glucose concentrations. In the GOP method, there is a limit to the number of measurements that can be made, because an electrode must be brought into contact with the sample and because of its principle of measurement; as a result, maintenance which involves replacing part of the measurement apparatus, adding a buffer solution, etc. must be performed periodically.

In contrast, in the optical rotation measuring method that uses a beam of light, as the measurement can be made without contacting the sample directly, the measurement apparatus can be used, without requiring any particular maintenance work, for a relatively long period of time. The period depends on the life of the light source, the degree of contamination of the sample cell, etc.

The optical method based on the optical rotation, etc. has the further advantage that there is no danger of a human subject accidentally touching the sample such as urine and the measurement can be done without making the subject particularly conscious of it.

The principle of the method that obtains the concentration of an optically active substance in a sample from the optical rotation produced by it is based on the following equation (1).

$$\theta(\lambda) = \alpha(\lambda) \cdot c \cdot L \tag{1}$$

where $\theta(\lambda)$ is the optical rotation when the wavelength of the light beam is denoted by $\lambda$, $\alpha(\lambda)$ is the specific rotation of the optically active substance when the wavelength of the light beam is denoted by $\lambda$, c is the concentration of the optically active substance in the sample, and L is the optical path length through the sample. In the equation 1, the specific rotation $\alpha(\lambda)$ is a coefficient unique to the optically active substance (though it varies depending on the wavelength $\lambda$ of the light beam or on temperature) and is therefore a value known before the measurement of the concentration. The optical path length L through the sample is also a value known before the measurement of the concentration. Accordingly, the concentration, c, of the optically active substance can be determined by measuring the optical rotation $\theta(\lambda)$ when the beam is passed through the sample.

Here, the optical rotation is obtained in the following manner: first, linearly polarized light is directed into the sample, and the light passed through the sample is input to an analyzer; then, the light passed through the analyzer is input to a photodetector such as a photodiode for conversion into an electrical signal, from which the optical rotation is obtained.

That is, when the tilt angle of the transmission axis of the analyzer with respect to the transmission axis of the polarizer is denoted by $\phi$, and the optical rotation produced by the sample is denoted by $\beta$, then the intensity, I, of the light received by the photodetector can be determined based on the following equation (2).

$$I = T \times I_0 \cos^2(\phi - \beta) \tag{2}$$

where T represents the transmittance considering all of the attenuations due to reflections and absorptions occurring in the sample, the polarizer, and the analyzer, and $I_0$ designates the intensity of the incident light. As can be understood from the equation (2), the intensity of light, I, changes as $\phi$ changes, and a minimum point is obtained for every rotation angle $\pi$(rad). Accordingly, the optical rotation $\beta$ produced by the sample can be obtained by measuring the intensity of light, I, when $\phi$ is changed.

One possible method to change $\phi$ would be to rotate the polarizer or the analyzer. However, the method of rotating the polarizer or the analyzer has had the problem that the apparatus size becomes relatively large, because it requires mechanical manipulation to rotate. In view of this, there is proposed a method that electrically modulates the plane of polarized light by using a Faraday element (for example, refer to patent document 1) or a liquid crystal element as a polarization rotator.

A Senarmont polarization rotator constructed by combining a liquid crystal element with a quarter-wave plate is an example that uses the liquid crystal element to rotate linearly polarized light. There is also proposed an apparatus in which three liquid crystal elements capable of being supplied with variable voltage are arranged in series along the direction of propagation of light, thereby achieving light modulation with greater freedom (for example, refer to patent document 2). Further, there is proposed an optical measurement apparatus that utilizes the optical characteristics of a liquid crystal element, eliminating the need for conventional mechanical moving parts (for example, refer to patent document 4). There is also proposed an apparatus that achieves highly accurate and stable measurements by periodically performing phase modulation using a liquid crystal element (for example, refer to patent document 3).

Further, when the sample is urine, a method is disclosed that detects a urine component by measuring its optical rotation (for example, refer to patent document 1).

FIG. 25 shows the optical system implementing the above method.

In FIG. 25, a beam of light emitted from a light source 21 such as a laser diode is collimated by a collimating lens 22 into a parallel beam of light, which is converted by a polarizer 23 into linearly polarized light vibrating in a vertical direction. The linearly polarized light passed through the polarizer 23 enters a liquid crystal element 31 where the polarization component in the direction of +45 degrees or −45 degrees relative to the vertical is phase-modulated. In the liquid crystal element 31, the long axes of the liquid crystal molecules are aligned in the direction of +45 degrees or −45 degrees (homogeneous alignment). The light passed through the liquid crystal element 31 emerges as elliptically polarized light, whose ellipticity varies with the voltage applied to the liquid crystal element 31.

The light passed through the liquid crystal element 31 is split by a beam splitter 24 into reflected light and rectilinearly propagating light. The rectilinearly propagating light enters a quarter-wave plate 26A whose axis is oriented in the vertical axis direction, and the light is thus converted to linearly polarized light. At this time, as the polarization direction of the linearly polarized light depends on the ellipticity of the light passed through the liquid crystal element 31, the polarization direction varies depending on the voltage applied to the liquid crystal element 31. In this way, the polarization direction of the linearly polarized light can be modulated by the liquid crystal element 31. When the linearly polarized light whose polarization direction is thus modulated enters the test sample, the polarization direction is rotated by an unknown amount in accordance with the optical activity of the sample. The light passed through the sample enters a quarter-wave plate 26B where it is converted back to elliptically polarized light, and the elliptically polarized light enters an analyzer 27A. Of the components of the incident light, only the component vibrating in the same direction as the transmission axis of the analyzer 27A is passed through the analyzer 27A. The light passed through the analyzer 27A falls on a photodetector 29A where the light is converted into an electrical signal.

The reflected light separated by the beam splitter 24 is not directed toward the sample but is directed to an analyzer 27B. The light passed through the analyzer 27B falls on a photodetector 29B where the light is converted into an electrical signal.

The difference between the output signal of the photodetector 29A and the output signal of the photodetector 29B corresponds to the difference between the elliptically polarized light before entering the analyzer 27A and the elliptically polarized light before entering the analyzer 27B (that is, the angle of optical rotation through the sample). Accordingly, the angle of optical rotation through the sample can be measured from the difference between the output signal of the photodetector 29A and the output signal of the photodetector 29B, and the concentration of component in the sample can be determined from the angle of optical rotation through the sample.

While the angle of optical rotation can be obtained by the above method, actual test samples often contain optically active components other than the optically active component of interest. For example, when measuring sugar in urine (glucose in urine), the urine may contain vitamin C (specific rotation: 23°) due, for example, to an intake of a nutritional supplement. Since the molecular weight of glucose (180) is close to that of vitamin C (176), it is difficult to separate one from the other by the size of molecules.

A method that uses test strips is commonly employed as a method for analyzing urine. This method uses test strips coated with reagents for testing various components; that is, the test strips are immersed in the urine collected in a paper cup or the like, and the components of the urine are analyzed by the reagents that change color through chemical reactions. The change of color is checked by visual inspection or by using an optical sensor.

Further, there is also a method that uses an enzyme electrode method for the measurement of urine sugar; in this method, glucose in the urine is caused to undergo a chemical reaction by glucose oxidase (GOP), and the urine sugar level is quantified by measuring the generated current.

Patent document 1: Japanese Unexamined Patent Publication No. H09-145605 (FIG. 1)

Patent document 2: Japanese Unexamined Patent Publication No. H07-218889 (FIG. 3)

Patent document 3: Japanese Unexamined Patent Publication No. 2002-277387 (FIG. 3)

Patent document 4: Japanese Unexamined Patent Publication No. 2001-356089 (FIG. 3)

SUMMARY OF THE INVENTION

It is accordingly an object of the present invention to provide an optical measurement apparatus that can solve the problem associated with the prior art.

It is another object of the present invention to provide an optical measurement apparatus equipped with an ion-exchange resin for pretreating a sample, thereby enabling the concentration of component in the sample to be measured with higher accuracy.

An optical measurement apparatus according to the present invention includes an ion-exchange resin, and an optical measurement section for measuring the concentration of component in a sample based on optical characteristics of the component after the sample is passed through the ion-exchange resin.

Preferably, the optical measurement apparatus according to the present invention further comprises a regenerating section for regenerating or cleaning the ion-exchange resin.

Preferably, in the optical measurement apparatus according to the present invention, the regenerating section regenerates the ion-exchange resin with alkaline ionized water, and further preferably, the regenerating section includes an alkaline ionized water producing section for producing the alkaline ionized water from tap water.

Preferably, in the optical measurement apparatus according to the present invention, the regenerating section regenerates the ion-exchange resin with acid water, and further preferably, the regenerating section includes an acid water producing section for producing the acid water from tap water.

Preferably, in the optical measurement apparatus according to the present invention, the regenerating section cleans the ion-exchange resin with tap water.

Preferably, in the optical measurement apparatus according to the present invention, the ion-exchange resin is replaceably mounted, and the ion-exchange resin is a weak base ion-exchange resin.

Preferably, the optical measurement apparatus according to the present invention further comprises a synthetic adsorbent, and the optical measurement apparatus makes the measurement after the sample is passed through the synthetic adsorbent and through the ion-exchange resin.

Preferably, in the optical measurement apparatus according to the present invention, the ion-exchange resin is filled into a column having a transparent window.

Preferably, the optical measurement apparatus according to the present invention further comprises a detecting section for detecting the color of the ion-exchange resin.

An optical measurement apparatus according to the present invention includes: an ion-exchange resin, a holding cell for temporarily holding a sample after the sample is passed through the ion-exchange resin, a measurement container for holding the sample for an optical measurement after the sample is passed through the ion-exchange resin, an optical measurement section for measuring the concentration of a component in the sample based on optical characteristics of the component when the sample is held in the measurement container; a detecting section for detecting the color of the ion-exchange resin through which the sample has been passed; a first liquid feeding means for feeding the sample held in the holding cell back to the ion-exchange resin in order to make the sample pass therethrough once again; and a second liquid feeding means for feeding the sample held in the holding cell into the measurement container.

An optical measurement apparatus according to the present invention includes: a first ion-exchange resin, a first holding cell for temporarily holding a sample after the sample is passed through the first ion-exchange resin, a second ion-exchange resin; a second holding cell for temporarily holding the sample after the sample is passed through the second ion-exchange resin, a measurement container for holding the sample for an optical measurement after the sample is passed through the first ion-exchange resin or through the first and second ion-exchange resins, an optical measurement section for measuring the concentration of component in the sample based on optical characteristics of the component when the sample is held in the measurement container, a detecting section for detecting the colors of the first and second ion-exchange resins through which the sample has been passed, a first liquid feeding means for feeding the sample held in the holding cell into the second ion-exchange resin in order to make the sample pass therethrough, a second liquid feeding means for feeding the sample held in the first holding cell into the measurement container, and a third liquid feeding means for feeding the sample held in the second holding cell into the measurement container.

An optical measurement apparatus according to the present invention includes: an ion-exchange resin, an optical measurement section for measuring the concentration of an optically active substance in a sample based on optical characteristics of the optically active substance after the sample is passed through the ion-exchange resin, and a control section for continuously monitoring a measurement result from the optical measurement section.

Preferably, in the optical measurement apparatus according to the present invention, the control section computes the concentration of the optically active substance by using the measurement result obtained when the measurement result has settled to a steady-state value.

Preferably, in the optical measurement apparatus according to the present invention, the control section makes a determination, based on the monitoring of the measurement result, as to whether the ion-exchange ability of the ion-exchange resin has become saturated or not.

Preferably, in the optical measurement apparatus according to the present invention, the sample is urine and the optically active substance is urine sugar.

Preferably, in the optical measurement apparatus according to the present invention, the ion-exchange resin is an anion-exchange resin, a mixed-bed ion-exchange resin, or a cation-exchange resin.

Preferably, the optical measurement apparatus according to the present invention further comprises a regenerating section for regenerating the ion-exchange resin with a regenerating solution, and the control section makes a determination, based on the monitoring of the measurement result, as to the degree to which the ion-exchange resin has been regenerated with the regenerating solution.

Preferably, in the optical measurement apparatus according to the present invention, the control section controls the amount of the regenerating solution.

The optical measurement apparatus according to the present invention is installed in a toilet seat or a toilet bowl.

The optical measurement apparatus according to the present invention is equipped with an ion-exchange resin and measures the concentration of component in a solution based on the optical characteristics thereof, wherein the concentration of component in the solution is measured by an optical system after the solution is passed through the ion-exchange resin.

Here, if provisions are made to regenerate the ion-exchange resin with alkaline ionized water, then the optical measurement apparatus is maintenance free, providing a more effective system. In particular, if the ion-exchange resin is a weak base ion-exchange resin, the apparatus can be used in a wide range of applications. When the solution to be analyzed is urine, and the apparatus is installed in a toilet seat or a toilet bowl, its effect is particularly great.

If the ion-exchange resin is replaceable, it can be replaced after use. Further, if a device for supplying the regenerating solution for regenerating the ion-exchange resin is provided in the toilet seat or toilet bowl, or if a device for producing alkaline ionized water or a device for producing acid water is provided in the toilet seat or toilet bowl, it facilitates the use of the apparatus in the toilet because the ion-exchange resin can be readily regenerated. If the ion-exchange resin is first washed with tap water and then regenerated with alkaline ionized water, its performance can be maintained for a long period of time. Similarly, if the ion-exchange resin is first washed with water and then regenerated with acid water, its performance can be maintained for a long period of time.

In the optical measurement apparatus which measures the concentration of an optically active substance in a sample by measuring the optical rotation produced by the optically active substance, the optical measurement for measuring, for example, the sugar level in the urine is performed after passing the urine through a weak base anion-exchange resin and thereby removing vitamin C contained in the urine due, for example, to an intake of a nutritional supplement. Vitamin C having a strong reducing power is adsorbed onto the weak base anion-exchange resin, but glucose is not adsorbed; that is, by passing the urine through the weak base anion-exchange resin, the sugar level in the urine with vitamin C removed from it can be measured.

When regenerating an OH type weak base anion-exchange resin, a specially prepared regenerating solution is not used, but alkaline ionized water is used that is produced by a water ionizer from tap water. That is, there is no need to use any special regenerating solution because tap water readily available in homes, offices, etc. can be used. This eliminates the need to replenish the solution, and offers a great advantage in terms of maintenance when the optical measurement apparatus of the present invention is installed in a toilet seat or a toilet bowl. In the case of an H type weak acid cation-exchange resin, acid water produced by a water ionizer from tap water is used as the regenerating solution.

In the optical measurement apparatus of the present invention, the optical rotation can be measured with high accuracy because the measurement is made after the sample is passed through the ion-exchange resin to remove any optically active component other than the target component.

Further, in the optical measurement apparatus of the present invention, no specially prepared regenerating solution but only an alkaline ionized water or an acid water produced by the water ionizer from tap water is used to regenerate the weak base anion-exchange resin and the weak acid cation-exchange resin. Accordingly, the apparatus is substantially free from maintenance. This is particularly effective when the optical measurement apparatus of the present invention is installed in a toilet seat or a toilet bowl where the tap water is readily available.

Furthermore, in the optical measurement apparatus of the present invention, as ions are removed from the sample, the sample holding section is less prone to contamination, and its light transmittance does not easily degrade, besides, washing can be done easily.

An optical measurement apparatus according to the present invention includes: means for removing, using an ion-exchange resin, an interfering substance that interferes with the measurement of the optical rotation produced by a target component in a sample, and monitoring means for continuously monitoring the optical rotation produced in the sample that has passed through the ion-exchange resin.

Preferably, the apparatus further comprises sensing means for sensing that the optical rotation being monitored by the monitoring means has reached a steady state, wherein the concentration of the target component in the sample is measured when the sensing means has sensed that the optical rotation being monitored has reached a steady state.

Also preferably, from the optical rotation being monitored by the monitoring means, the sensing means senses that the ion-exchange ability of the ion-exchange resin has become saturated.

Further preferably, after the sensing means has sensed that the ion-exchange ability of the ion-exchange resin has saturated, the concentration of the optically active substance in the sample is measured when the sensing means has sensed that the optical rotation being monitored has reached a steady state.

The optical measurement apparatus of the present invention is particularly useful when the sample is urine and the target component is urine sugar.

Preferably, the ion-exchange resin is an anion-exchange resin, a mixed-bed ion-exchange resin, or a cation-exchange resin.

Preferably, the amount of sample necessary for measurement is managed through feedback control by the monitoring means.

Preferably, the completion of the regeneration of the ion-exchange resin is managed through feedback control during the continuous measurement being performed in the optical measurement apparatus of the present invention.

In the optical measurement apparatus which measures the sugar level in the urine by measuring the optical rotation produced through the urine, the ion-exchange resin is useful for removing optically active substances other than urine sugar. There is, however, a need to prevent the measurement accuracy from dropping due to the dilution of the urine with the preservative solution used to moisten the ion-exchange resin. For this purpose, the monitoring means constantly monitors changes in the optical rotation by continuously monitoring the optical rotation produced in the sample that has been passed through the ion-exchange resin, and the concentration of urine sugar is measured after detecting that the optical rotation has reached a steady state; in this way, the concentration of urine sugar can be measured with high accuracy.

In the optical measurement apparatus having the ion-exchange resin according to the present invention, the concentration can be measured with good accuracy by providing the optical rotation monitoring means and sensing means.

Further, in the optical measurement apparatus according to the present invention, as the optical rotation before the ion exchange of the sample can also be measured by the continuous monitoring means and the optical rotation measurement, the optical rotation produced by optically active substances other than urine sugar can also be obtained by subtracting the optical rotation before the ion exchange from the optical rotation after the ion exchange.

Further, in the optical measurement apparatus according to the present invention, the amount of sample necessary for measurement can be controlled and managed by the continuous monitoring means.

Further, in the optical measurement apparatus according to the present invention, the completion of the regeneration of the ion-exchange resin can be controlled and managed by the continuous monitoring means.

An optical measurement apparatus according to the present invention includes, ion removing means constructed from a plurality of regions with a partitioning membrane made of an ion-exchange membrane separating one region from another, each region being filled with an ion exchange resin and being provided with an electrode to which a voltage is applied, and optical rotation measuring means for measuring the optical rotation in a sample after the sample is passed through the ion removing means.

Preferably, in the optical measurement apparatus according to the present invention, the ion-exchange resin comprises a mixed bed of anion-exchange and cation-exchange resins.

An optical measurement apparatus according to the present invention includes: ion removing means having a sample chamber and a waste solution chamber, one separated from the other by a partitioning membrane made of an ion-exchange membrane, wherein the sample chamber is, or both the sample chamber and the waste solution chamber are, filled with an ion-exchange resin, and the sample chamber or the waste solution chamber is provide with an electrode to which a voltage is applied; and optical rotation measuring means for measuring the optical rotation in a sample after the sample is passed through the ion removing means.

Preferably, in the optical measurement apparatus according to the present invention, the partitioning membrane is made of an anion-exchange membrane, and the sample chamber has a negative electrode and an anion-exchange resin.

Preferably, in the optical measurement apparatus according to the present invention, the partitioning membrane is made of a cation-exchange membrane, and the sample chamber has a positive electrode and a cation-exchange resin.

Preferably, in the optical measurement apparatus according to the present invention, the electrode, the sample chamber, and the waste solution chamber are arranged in a concentric relation to each other when viewed in cross section.

Preferably, in the optical measurement apparatus according to the present invention, the ion removing means comprises an ion removal section filled with an anion-exchange resin and an ion removal section filled with a cation-exchange resin, wherein the sample passes through the two ion removal sections in a serial fashion.

Preferably, in the optical measurement apparatus according to the present invention, a solution for controlling the temperature of the optical rotation measuring means is utilized as a solution into which an interfering substance contained in the sample is discharged, and heat exchange is performed between the two solutions to make the temperature of the sample substantially the same as the temperature of the optical rotation measuring means.

In the optical measurement apparatus according to the present invention, the interfering substance contained in the sample is ionized, which is then removed by the ion removing means, and the optical rotation produced through the sample is measured after the sample is passed through the ion removing means, in this way, the concentration of the target component in the sample can be measured. For example, when the sample is urine, urine sugar can be quantified by removing the amino acids contained in the urine.

Further, in the optical measurement apparatus according to the present invention, when a mixed bed of anion-exchange and cation-exchange resins is used as the ion-exchange resin filled into the ion removing means, both positive and negative ions can be removed.

In the optical measurement apparatus according to the present invention, the ion removing means is provided with electrodes, and when a voltage is applied between the electrodes, a reduction reaction occurs at the negative electrode, while an oxidation reaction occurs at the positive electrodes. The actual reactions that occur differ depending on the electrode material and the kind of ions dissolved in the sample, but when platinum electrodes are used, and there are no $Cl^-$ ions in the solution, then at the negative electrode $H^+$ ions are reduced to from $H_2$, while at the positive electrode, $OH^-$ ions are oxidized to generate $O_2$. As a result, at the negative electrode, the pH shifts into the alkaline range, while at the positive electrode, the pH shifts into the acid range, and the pH can thus be adjusted. Therefore, various kinds of amino acids which form dipolar ions can be ionized.

For example, when the ion removing means is divided into two regions separated by a partitioning membrane, and a negative electrode and a positive electrode are provided in the respective regions, the negative electrode side being filled with an anion-exchange resin and the positive electrode side with a cation-exchange resin, then when a voltage is applied causing the pH at the negative electrode side to shift into the alkaline range, amino acids as dipolar ions turn into negative ions which can be adsorbed onto the anion-exchange resin. On the other hand, at the positive electrode side, the pH shifts into the acid range, and amino acids are turned into positive ions which can be adsorbed onto the cation-exchange resin.

Further, in the optical measurement apparatus according to the present invention, the adsorbed ions move under the influence of an electric field, and the ions are thus drained to the outside through the partitioning membrane, accomplishing the regeneration of the ion-exchange resin. When an ion-exchange membrane is used as the partitioning membrane, the regeneration of the ion-exchange resin can be performed while preventing the infiltration of ions opposite in polarity to the ions being drained, and thus permitting continuous removal of interfering substances.

In this way, in the optical measurement apparatus according to the present invention, by applying an electric field, the pH can be adjusted and the interfering substances can be adsorbed onto the ion-exchange resin for removal, thus accomplishing the regeneration of the ion-exchange resin while permitting continuous removal of the interfering substances.

In the optical measurement apparatus according to the present invention, when the temperature control solution for controlling the temperature of the sensor section that measures the optical rotation is also used as the waste solution into which the ions adsorbed on the ion-exchange resin are discharged, and heat exchange is performed between the sample and the waste solution to make the temperature of the sample substantially the same as that of the sensor section then, when the sample is introduced into the sensor section a temperature change does not occur, preventing measurement errors from occurring due to a temperature change when measuring the optical rotation, and thus the concentration of component can be measured stably with high accuracy.

In this way, in the optical measurement apparatus according to the present invention, by passing the sample through the ion-exchange resin before introducing it into the sensor section for the measurement of the optical rotation, the concentration of component in the sample can be measured after removing interfering substances from the sample.

DETAILED DESCRIPTION OF THE PREFERRED EMBODIMENT

An optical measurement apparatus according to the present invention will be described below with reference to the drawings.

Figure 1:
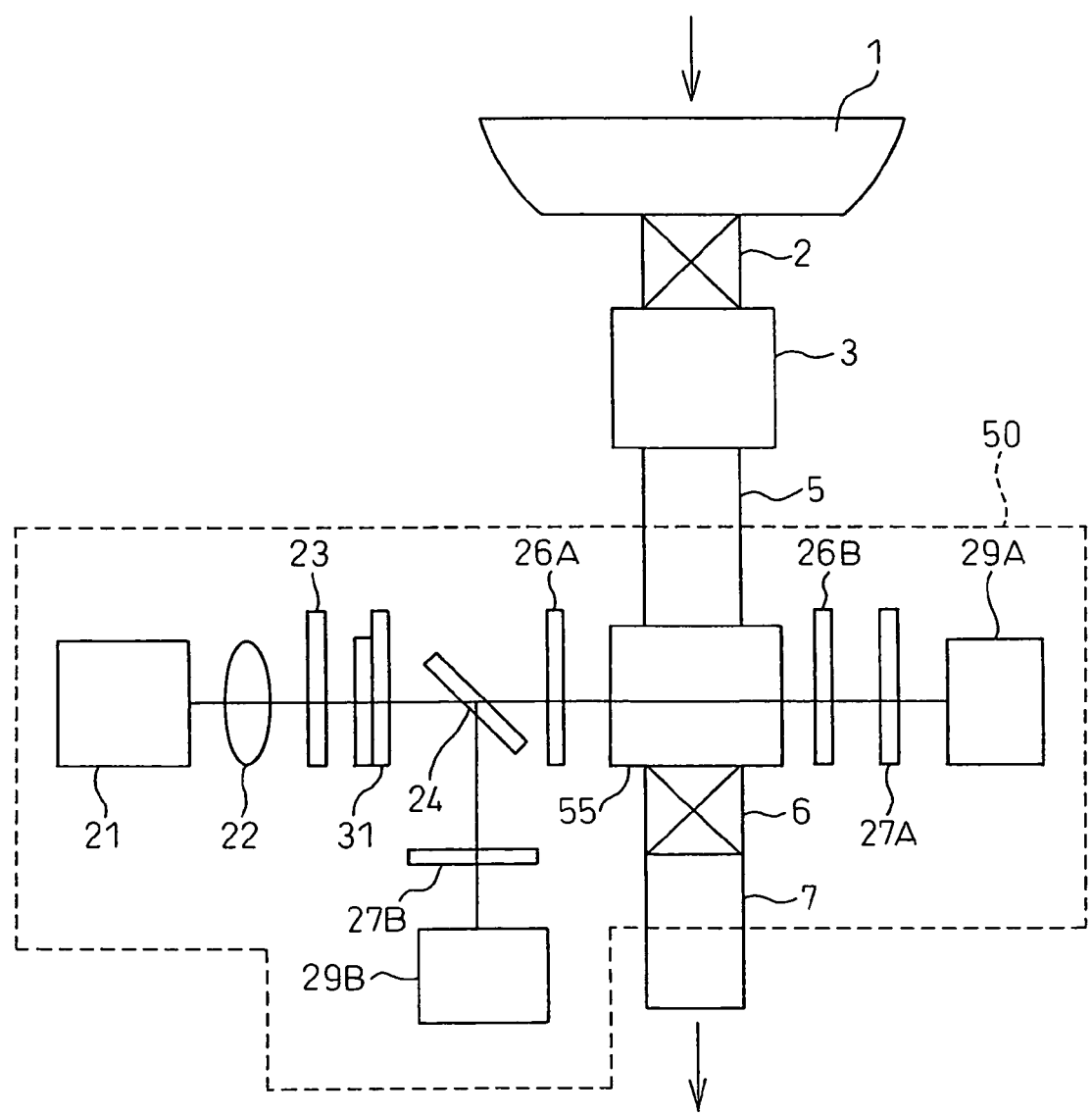
FIG. 1 is a diagram schematically showing the configuration of an optical measurement apparatus according to a first embodiment of the present invention.

FIG. 1 is a diagram schematically showing the configuration of an optical measurement apparatus according to a first embodiment of the present invention.

Figure 25:
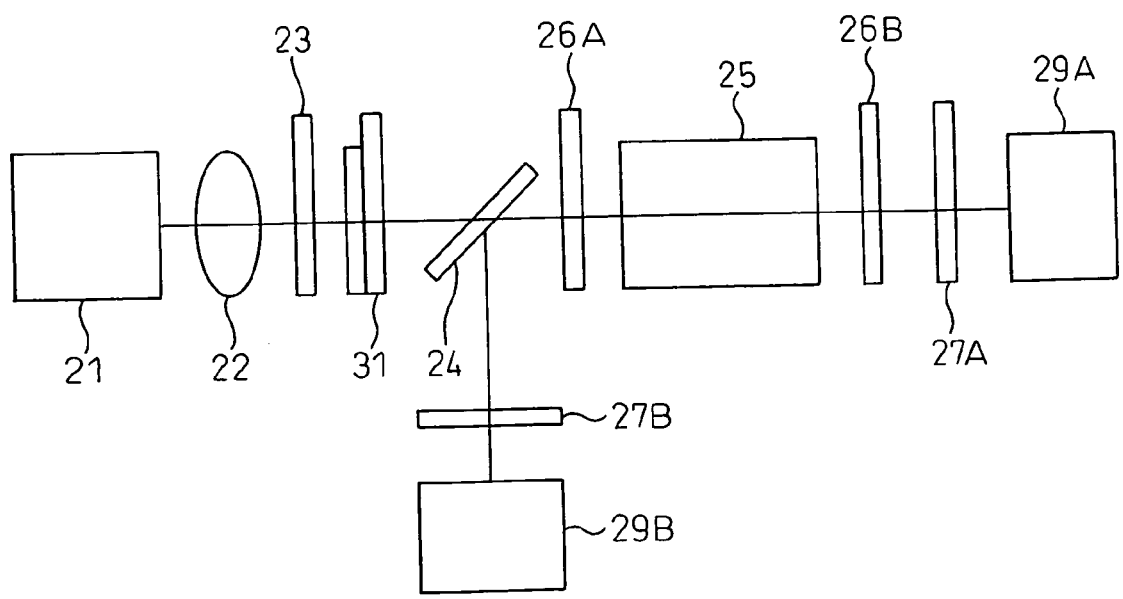
FIG. 25 is a diagram schematically showing the configuration of an optical measurement apparatus.

In FIG. 1, a urine collection container 1 is a container for collecting urine, and an electromagnetic valve 2 is provided between the urine collection container 1 and an ion-exchange resin section 3 and is actuated so as not to pass more than a prescribed amount of urine therethrough. The ion-exchange resin section 3 holds therein a weak base anion-exchange resin (for example, WA20 manufactured by Mitsubishi Chemical Corporation) which is detachable. A tube 5 connects between the ion-exchange resin section 3 and a measurement container 55, and conveys the urine therethrough. An electromagnetic valve 6 is provided between the measurement container 55 and a tube 7 and is opened after making a measurement of the urine sample. After the measurement is made, the urine sample is discharged through the tube 7. An optical system 50 is a system for measuring optical rotation, and components identical to those in the optical system shown in FIG. 25 are designated by the same reference numerals.

When urine is collected in the urine collection container 1, the electromagnetic valve 2 is opened, allowing the urine to flow into the ion-exchange resin section 3. At this time, glucose in the urine passes through this section, but vitamin C having a strong reducing power is removed by the weak base anion-exchange resin contained in the ion-exchange resin section 3. The reaction supposed to occur at this time is shown by the following chemical equation (3).

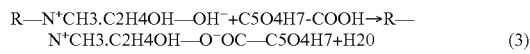

$$R—N^+CH3.C2H4OH—OH^- + C5O4H7\text{-}COOH \rightarrow R—N^+CH3.C2H4OH—O^-OC—C5O4H7 + H2O \quad (3)$$

Here, R indicates a styrene or divinylbenzene copolymer (DVB) as a polymer substrate.

The urine then passes through the tube 5 and is collected in the measurement container 55, and the optical rotation is measured by the optical system 50 as will be described below.

A beam of light emitted from a laser diode 21 is collimated by a lens 22 into a parallel beam of light. The parallel beam of light is converted by a polarizer 23 into linearly polarized light vibrating in a direction tilted by 45° with respect to the vertical direction. The linearly polarized light passed through the polarizer 23 enters a liquid crystal element 31 where the polarization component in either the horizontal or the vertical direction is phase-modulated. The liquid crystal element 31 is a liquid crystal element of homogeneous alignment in which the long axes of the liquid crystal molecules are aligned in the horizontal or vertical direction. When a voltage is applied to the liquid crystal element 31, the liquid crystal molecules stand up, and the refractive index in the molecular long axis direction changes; phase modulation can thus be performed.

Here, when phase modulation is applied to only one of the polarization components by the liquid crystal element 31, the mutually perpendicular polarization components interfere with each other.

The light passed through the liquid crystal element 31 is split by a beam splitter 24 into reflected light and rectilinearly propagating light. The rectilinearly propagating light enters a quarter-wave plate 26A whose axis is oriented in the vertical axis direction, and the light is thus converted to linearly polarized light. At this time, since the polarization direction of the linearly polarized light depends on the ellipticity of the light passed through the liquid crystal element 31, the polarization direction varies depending on the voltage applied to the liquid crystal element 31. In this way, the polarization direction of the linearly polarized light can be modulated by the liquid crystal element 31. When the linearly polarized light whose polarization direction is thus modulated enters the test sample, the polarization direction is rotated by an unknown amount in accordance with the optical activity of the sample. The light passed through the sample enters a quarter-wave plate 26B where it is converted back to elliptically polarized light, and the elliptically polarized light enters an analyzer 27A. Of the components of the incident light, only the component vibrating in the same direction as the transmission axis of the analyzer 27A is passed through the analyzer 27A. The light passed through the analyzer 27A falls on a photodetector 29A where the light is converted into an electrical signal.

The reflected light separated by the beam splitter 24 is not directed toward the sample but is directed to an analyzer 27B. The light passed through the analyzer 27B falls on a photodetector 29B where the light is converted into an electrical signal.

The difference between the output signal of the photodetector 29A and the output signal of the photodetector 29B corresponds to the difference between the elliptically polarized light before entering the analyzer 27A and the elliptically polarized light before entering the analyzer 27B (that is, the angle of optical rotation through the sample). Accordingly, the angle of optical rotation through the sample can be measured from the difference between the output signal of the photodetector 29A and the output signal of the photodetector 29B, and the concentration of a component in the sample can be determined from the angle of optical rotation through the sample.

Since vitamin C is removed from the urine as it passes through the ion-exchange resin section 3, the optical rotation through the urine substantially corresponds to the glucose concentration. When the measurement is completed, the second electromagnetic valve 6 is opened, and the urine is discharged through the tube 7.

The present embodiment has been described for the case where urine sugar is optically measured after removing vitamin C from the urine. It will, however, be appreciated that the optical measurement apparatus of the present invention may be used to measure sugar levels in fruits, etc. and the measurement target is not limited to urine. Further, vitamin C has been chosen as the component to be removed and glucose as the component to be measured, but the component to be removed need not be limited to vitamin C, and amino acids or the like may be taken as components to be removed. In the present embodiment, a weak base anion-exchange resin has been used as the ion-exchange resin, but alternatively, a strong base anion-exchange resin, a weak acid cation-exchange resin, a strong acid cation-exchange resin, etc. may be used. If necessary, these ion-exchange resins may be suitably combined for use.

The present embodiment has employed the method that passes the sample through the ion-exchange resin section 3. However, a batch method that causes the sample to react with the ion-exchange resin by agitation, etc. may be employed in order to maximize the performance of the ion-exchange resin.

In the present embodiment, the sample passed through the ion-exchange resin section 3 is fed directly into the measurement container 55. However, a membrane filter or a depth filter such as a glass fiber filter may be provided at the inlet or outlet of the ion-exchange resin section 3. The sample may become turbid due to a change in pH or due to reaction with the ion-exchange resin; if this happens, in the optical measurement the result of the measurement may vary due to the scattering of light caused by the turbid sample. In this case, if a depth filter or a membrane filter is provided to remove the turbidity, the measurement accuracy can be further enhanced.

Figure 2:
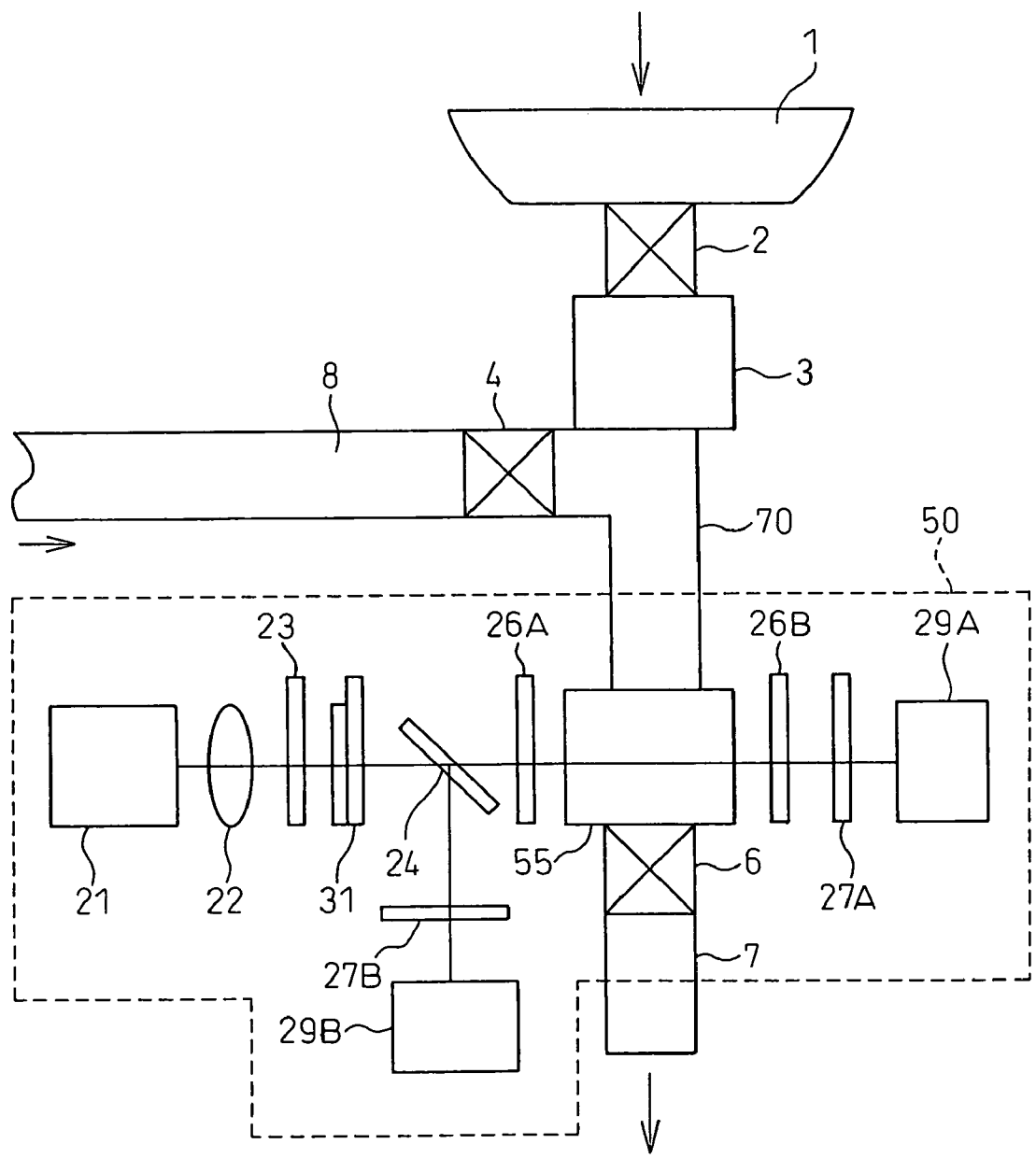
FIG. 2 is a diagram schematically showing the configuration of an optical measurement apparatus according to a second embodiment of the present invention.

FIG. 2 is a diagram schematically showing the configuration of an optical measurement apparatus according to a second embodiment of the present invention.

In FIG. 2, the urine collection container 1, the electromagnetic valve 2, and the optical system 50 are identical in configuration to those in the optical measurement apparatus described in the first embodiment. A tube 8 is provided between a tap water faucet and an electromagnetic valve 4, and it conveys tap water therethrough. The electromagnetic valve 4 is provided between the tube 8 and a tube 70 and is actuated to control the flow of water.

When urine is collected in the urine collection container 1, the electromagnetic valve 2 is opened, allowing the urine to flow into the ion-exchange resin section 3. As in the first embodiment, vitamin C in the urine is removed as it passes through the ion-exchange resin section 3. After that, the urine passes through the tube 70 and is collected in the measurement container 55, where the optical rotation is measured by the optical system 50. When the measurement is completed, the electromagnetic valve 6 is opened, and the measured urine is discharged to the outside.

Thereafter, the electromagnetic valve 6 is closed and, while leaving the electromagnetic valve 2 opened, the electromagnetic valve 4 is opened. The measurement container 55, the tube 70, the ion-exchange resin section 3, the electromagnetic valve 2, and the urine collection container 1 are thus washed with the tap water. In particular, in the ion-exchange resin section 3, as the tap water flows into the ion-exchange resin section 3 in the direction opposite to the direction in which the sample entered the ion-exchange resin section 3 (backwashing), the washing can be done effectively.

When the washing is completed, the electromagnetic valve 4 is closed, and the electromagnetic valve 6 is opened, allowing the tap water remaining in the measurement container 55, the tube 70, the ion-exchange resin section 3, the electromagnetic valve 2, and the urine collection container 1 to be discharged through the tube 7.

With the above structure and operation, highly effective washing can be accomplished. In the present embodiment, tap water has been used, but pure water or a specially prepared cleaning solution may be used.

Figure 3:
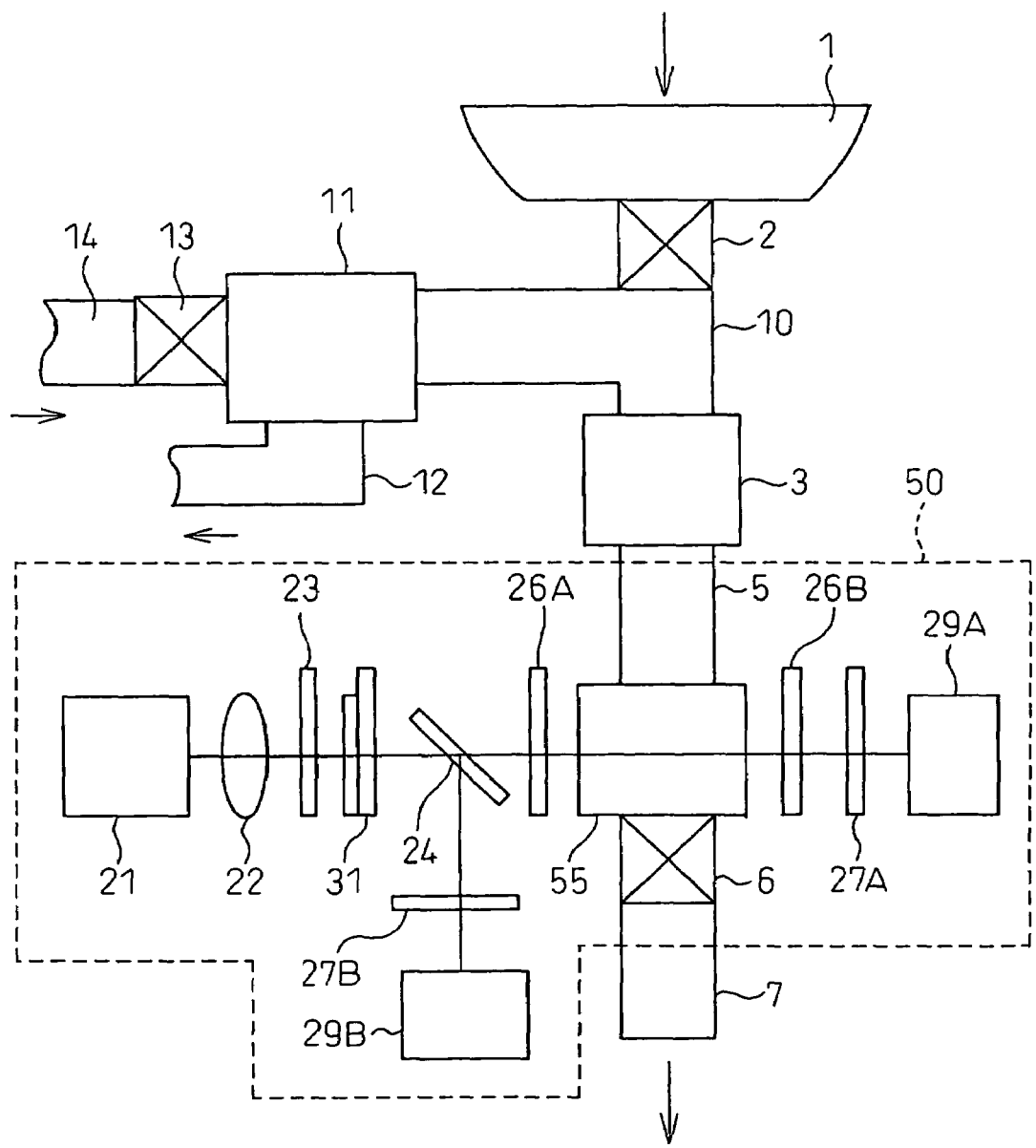
FIG. 3 is a diagram schematically showing the configuration of an optical measurement apparatus according to a third embodiment of the present invention.

FIG. 3 is a diagram schematically showing the configuration of an optical measurement apparatus according to a third embodiment of the present invention.

In FIG. 3, the urine collection container 1, the electromagnetic valve 2, and the optical system 50 are identical in configuration to those in the optical measurement apparatus described in the first embodiment. A tube 14 is provided between a tap water faucet and a water ionizer 11, and directs tap water into the water ionizer 11. The water ionizer 11 is a device for producing alkaline ionized water and acid water from the tap water, and is provided between an electromagnetic valve 13 and a tube 10. A tube 12 is provided to drain the acid water produced by the water ionizer 11. The electromagnetic valve 13 is provided between the tube 14 and the water ionizer 11 and controls the flow of the tap water to the water ionizer 11. The tube 10 is provided between the water ionizer 11, the electromagnetic valve 13, and the ion-exchange resin section 3, and directs the alkaline ionized water into the ion-exchange resin section 3.

When urine is collected in the urine collection container 1, the electromagnetic valve 2 is opened, allowing the urine to flow into the ion-exchange resin section 3. As in the first embodiment, vitamin C in the urine is trapped in the ion-exchange resin section 3. After that, the urine passes through the tube 5 and is collected in the measurement container 55, where the optical rotation is measured by the optical system 50. When the measurement is completed, the electromagnetic valve 6 is opened, and the measured urine is discharged outside.

Thereafter, the electromagnetic valve 13 is opened, and alkaline ionized water is produced by the water ionizer 11 and fed into the tube 10. That is, the alkaline ionized water flows into the ion-exchange resin section 3, and the exchange of OH⁻ ions occurs between the alkaline ionized water and the weak base anion-exchange resin, thus regenerating the ion-exchange resin section 3. The reaction supposed to occur at this time is shown by the following chemical equation (4).

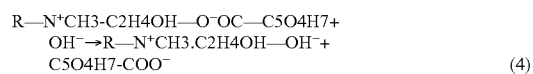

(4)

Here, R indicates a styrene or divinylbenzene copolymer (DVB) as a polymer substrate.

After a prescribed time has elapsed, the electromagnetic valves 13 and 6 are closed.

With the above structure and operation, the ion-exchange resin can be regenerated with tap water.

The present embodiment has used tap water, but pure water, purified water, or a specially prepared regenerating solution may be used instead. However, in applications where the optical measurement apparatus of the present invention is built into a toilet seat or a toilet bowl, as tap water is readily available, it is advantageous to use tap water because then there is no need to replenish the regenerating solution. Furthermore, in the present embodiment, as a weak base anion-exchange resin is used as the ion-exchange resin, alkaline ionized water has been used as the regenerating solution, but when a weak acid cation-exchange resin is used, it is preferable to use the acid water produced by the water ionizer 11 as the regenerating solution and to exchange ions for H⁺ ions. Assuming, for example, that the target to be removed by the ion-exchange resin is a positively ionized amino acid (R'—CHN+H3COOH), the reaction supposed to occur with the acid water is shown by the following chemical equation (5).

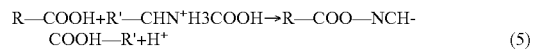

(5)

Here, R indicates a styrene or divinylbenzene copolymer (DVB) as a polymer substrate, and R' an organic molecule unique to each amino acid.

In the present embodiment, not only a weak base anion-exchange resin but also a strong base anion-exchange resin can be used.

Figure 4:
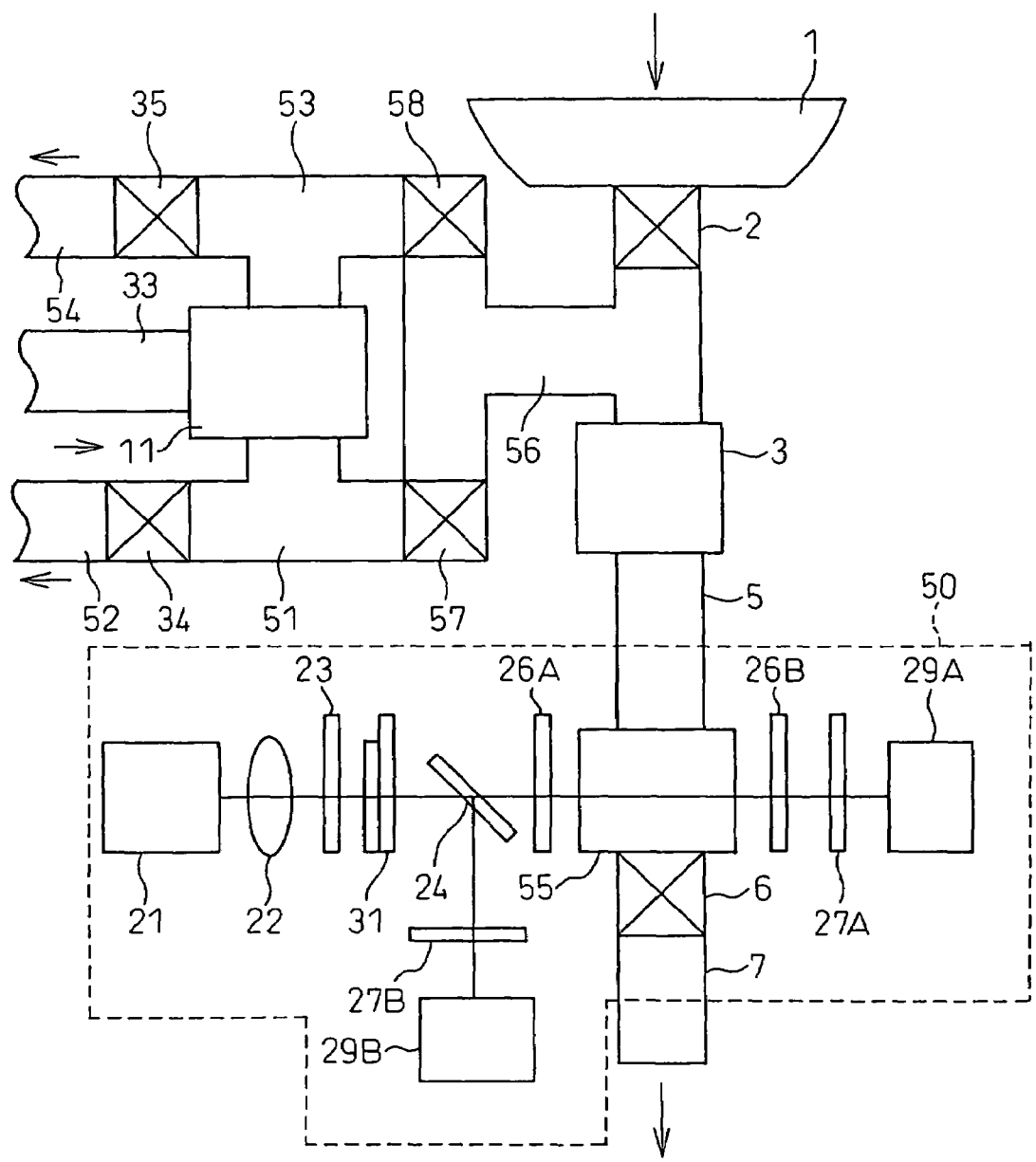
FIG. 4 is a diagram schematically showing the configuration of an optical measurement apparatus according to a fourth embodiment of the present invention.

FIG. 4 is a diagram schematically showing the configuration of an optical measurement apparatus according to a fourth embodiment of the present invention.

In FIG. 4, the urine collection container 1, the electromagnetic valve 2, and the optical system 50 are identical in configuration to those in the optical measurement apparatus described in the first embodiment. A tube 33 is provided between a tap water faucet and a water ionizer 11, and directs tap water into the water ionizer 11. The water ionizer 11 produces alkaline ionized water and acid water from the tap water.

A tube 51 is provided between the water ionizer 11 and electromagnetic valves 34 and 57, and conveys therethrough the acid water produced by the water ionizer 11. A tube 52 is connected to the electromagnetic valve 34 and drains the acid water. A tube 53 is provided between the water ionizer 11 and electromagnetic valves 35 and 58, and conveys therethrough the alkaline ionized water produced by the water ionizer 11. A tube 54 is connected to the electromagnetic valve 35 and drains the alkaline ionized water. A tube 56 is provided between the ion-exchange resin section 3 and the electromagnetic valves 57, 58, and 2, and directs the acid water and the alkaline ionized water into the ion-exchange resin section 3 to regenerate the weak base anion-exchange resin and weak acid cation-exchange resin contained in the ion-exchange resin section 3. The ion-exchange resin section 3 contains the weak base anion-exchange resin and the weak acid cation-exchange resin in order to remove negative as well as positive ion components.

When urine is collected in the urine collection container 1, the electromagnetic valve 2 is opened, allowing the urine to flow into the ion-exchange resin section 3. Vitamin C in the urine is removed by the weak base anion-exchange resin in the ion-exchange resin section 3, while basic amino acids in the urine are removed by the weak acid cation-exchange resin in the ion-exchange resin section 3. After that, the urine passes through the tube 5 and is collected in the measurement container 55, where the optical rotation is measured by the optical system 50. When the measurement is completed, the electromagnetic valve 6 is opened, and the measured urine is discharged outside.

Thereafter, the electromagnetic valve 6 is closed and the electromagnetic valve 58 is opened, while leaving the electromagnetic valve 57 closed and electromagnetic valve 34 opened; in this condition, the alkaline ionized water produced by the water ionizer 11 is fed into the tube 56. That is, by passing the alkaline ionized water into the ion-exchange resin section 3, the weak base anion-exchange resin in the ion-exchange resin section 3 is regenerated. The reaction supposed to occur at this time is the same as that shown by the earlier given chemical equation (4).

Next, the electromagnetic valve 58 is closed, and the electromagnetic valve 35 is opened while, on the other hand, the electromagnetic valve 34 is closed and the electromagnetic valve 57 is opened; in this condition, the acid water produced by the water ionizer 11 is fed into the tube 56. That is, by passing the acid water into the ion-exchange resin section 3, the weak acid cation-exchange resin in the ion-exchange resin section 3 is regenerated. When the target to be removed by the ion-exchange resin section 3 is a positively ionized amino acid (R'—CHN+H3COOH), the reaction supposed to occur at this time is as shown by the following chemical equation (6).

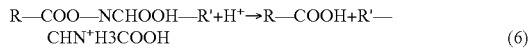

R—COO—NCHOOH—R'+H$^+$→R—COOH+R'—CHN$^+$H3COOH  (6)

Here, R indicates a styrene or divinylbenzene copolymer (DVB) as a polymer substrate, and R' an organic molecule unique to each amino acid.

As described above, according to the optical measurement apparatus of the present embodiment, both the cation-exchange resin and the anion-exchange resin can be regenerated with tap water. Further, the optical measurement apparatus of the present embodiment can also be used for conditioning the ion-exchange resins by acids and alkalis. In applications where the optical measurement apparatus of the present invention is built into a toilet seat or a toilet bowl, as tap water is readily available it is particularly advantageous to use tap water because then there is no need to replenish the regenerating solution. The present embodiment has been described as using a weak base anion-exchange resin and a weak acid cation-exchange resin, but a strong base anion-exchange resin or a strong acid cation-exchange resin may be used instead.

In the present embodiment, it is also possible to use a resin having both cation and anion exchange groups.

Further, the optical measurement apparatus of the present embodiment has been described as having a configuration for regenerating the ion-exchange resins, but rather than the resins being regenerated, the resin container may be replaced after each measurement (or after a predetermined number of measurements) or at every predetermine time interval.

Figure 5:
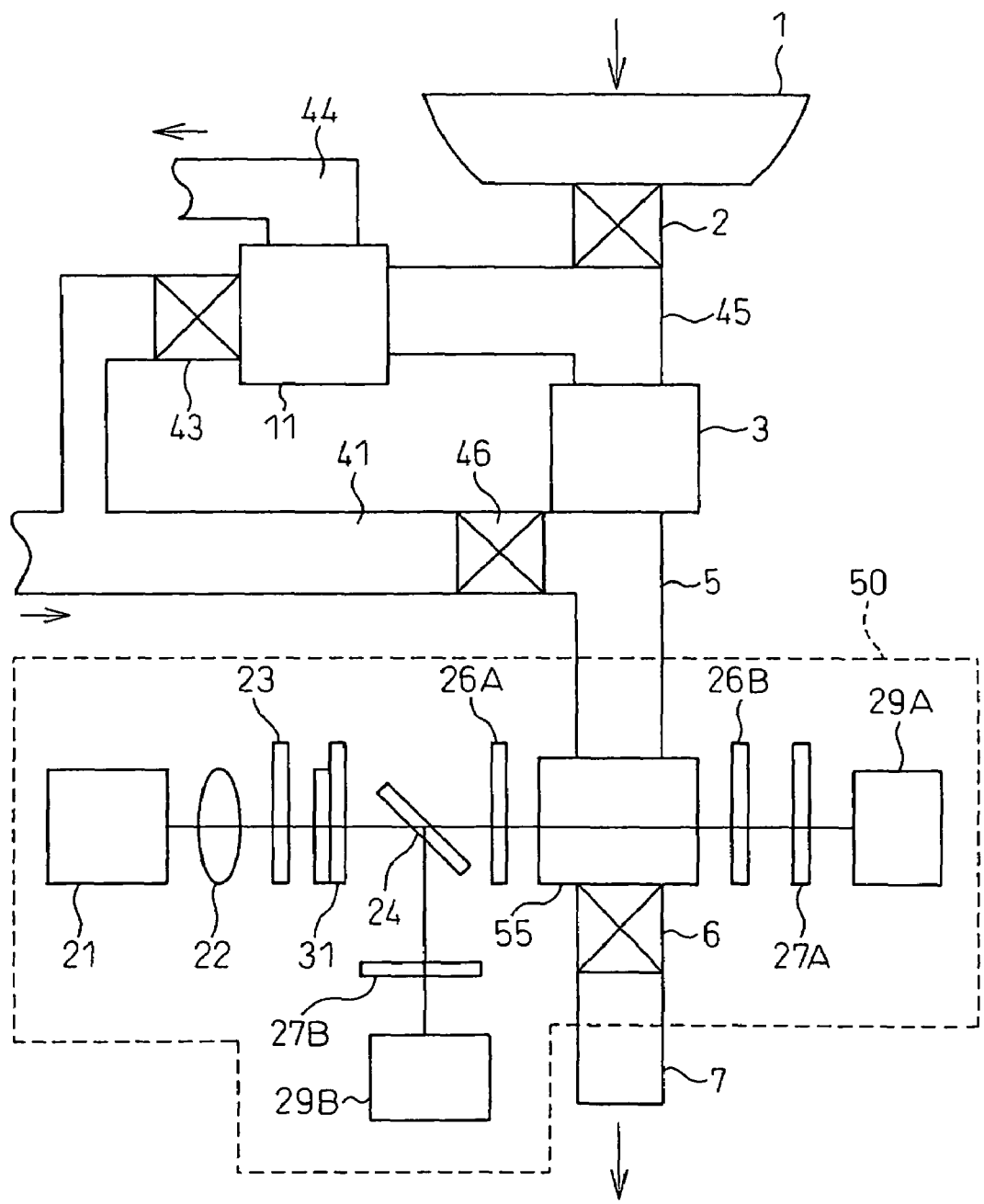
FIG. 5 is a diagram schematically showing the configuration of an optical measurement apparatus according to a fifth embodiment of the present invention.

FIG. 5 is a diagram schematically showing the configuration of an optical measurement apparatus according to a fifth embodiment of the present invention.

In FIG. 5, the urine collection container 1, the electromagnetic valve 2, and the optical system 50 are identical in configuration to those in the optical measurement apparatus described in the first embodiment. A tube 41 is provided, between a tap water faucet, a water ionizer 11, and an electromagnetic valve 46, and it directs tap water into the water ionizer 11 and also into the ion-exchange resin section 3 for washing. The water ionizer 11 produces alkaline ionized water and acid water from the tap water.

An electromagnetic valve 43 is provided between the tube 41 and the water ionizer 11, and introduces the tap water into the water ionizer 11. A tube 44 is connected to the water ionizer 11 and drains the acid water. A tube 45 is provided between the water ionizer 11, the electromagnetic valve 2, and the ion-exchange resin section 3, and directs the alkaline ionized water into the ion-exchange resin section 3 to regenerate the weak base anion-exchange resin contained in the ion-exchange resin section 3.

When urine is collected in the urine collection container 1, the electromagnetic valve 2 is opened, allowing the urine to flow into the ion-exchange resin section 3. As in the first embodiment, vitamin C in the urine is removed as it passes through the ion-exchange resin section 3. After that, the urine passes through the tube 5 and is collected in the measurement container 55, where the optical rotation is measured by the optical system 50. When the measurement is completed, the electromagnetic valve 6 is opened, and the measured urine is discharged through the tube 7.

Thereafter, the electromagnetic valve 46 is opened, and the tap water is fed through the tube 41. That is, by passing the tap water into the ion-exchange resin section 3, the weak base anion-exchange resin contained in the ion-exchange resin section 3 is washed. Then, the electromagnetic valve 46 is closed, the electromagnetic valve 43 is opened, and the alkaline ionized water generated by the water ionizer 11 is fed into the tube 45. That is, by passing the alkaline ionized water into the ion-exchange resin section 3, the weak base anion-exchange resin contained in the ion-exchange resin section 3 is regenerated.

According to the optical measurement apparatus of the present embodiment, washing and regeneration can be accomplished using tap water. In applications where the optical measurement apparatus of the present invention is built into a toilet seat or a toilet bowl, as tap water is readily available, it is particularly advantageous to use tap water because then there is no need to replenish the regenerating solution. The present embodiment has been described as using a weak base anion-exchange resin, but a weak acid cation-exchange resin or an ordinary base anion-exchange resin or acid cation-exchange resin may be used instead.

Further, EDI (Electronic De-Ionization) technology, as employed in a water purification system, may be used as a device for regenerating the ion-exchange resin section 3.

In the first to fifth embodiments described above, a liquid crystal element has been used as the polarization rotator in the optical rotation measurement apparatus, but alternatively, a Faraday element or the like may be used as the optical rotation modulating means. In that case also, effects similar to those achieved in the first to fifth embodiments can be obtained. Further, the first to fifth embodiments have each been described as using an optical system for measurement of the optical rotation. However, the optical measurement system of the present invention may be an optical system for the measurement of other optical properties (for example, the measurement of optical absorption), and components interfering with the intended measurement may be removed in collaboration with the ion-exchange resin.

In the first to fifth embodiments described above, it is preferable that the operation of each valve be controlled in accordance with a prescribed program by a controller comprising a PC or a CPU or the like, not shown.

Figure 6:
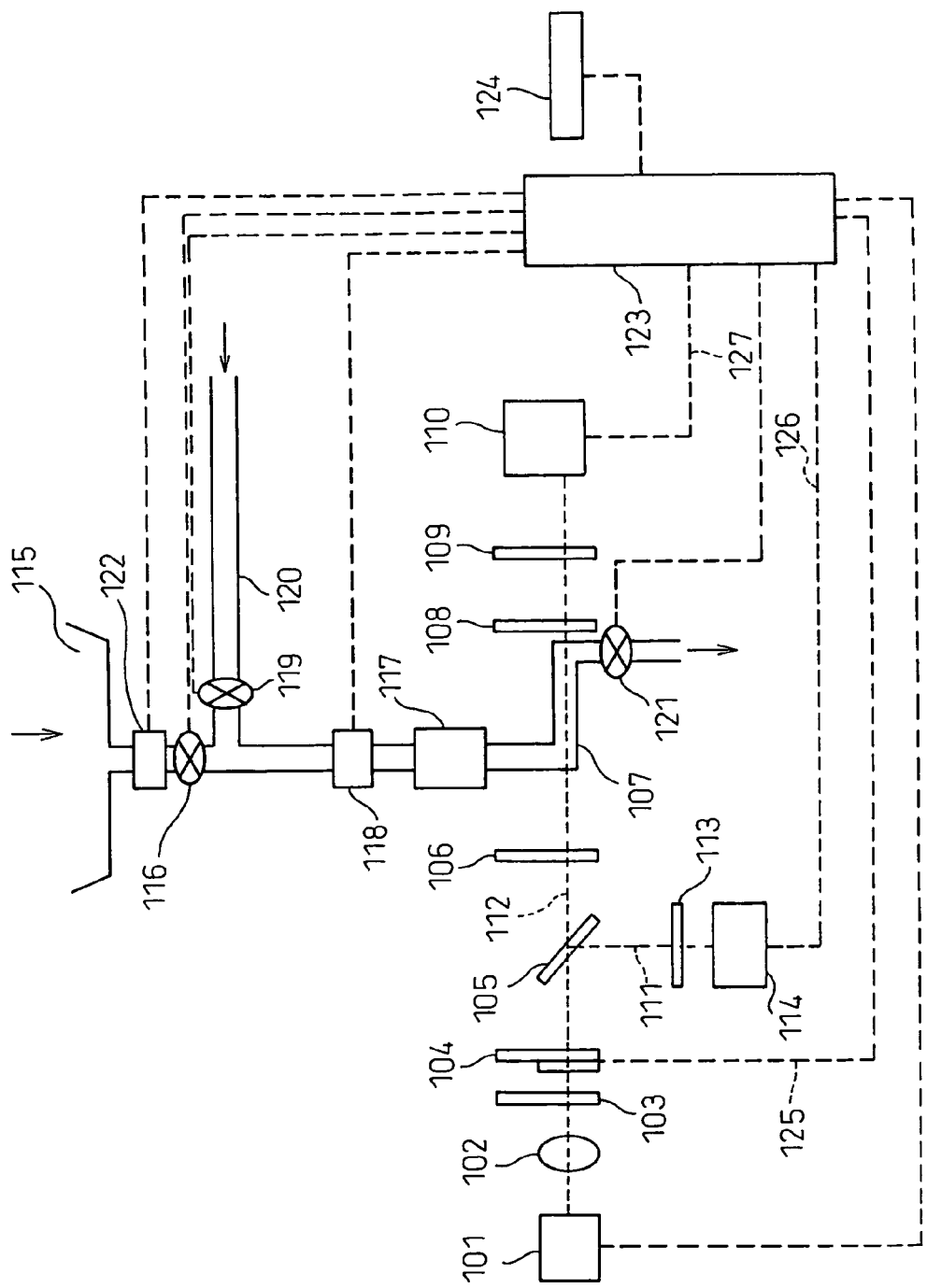
FIG. 6 is a diagram schematically showing the configuration of an optical measurement apparatus according to a sixth embodiment of the present invention.

FIG. 6 is a diagram schematically showing the configuration of an optical measurement apparatus according to a sixth embodiment of the present invention.

In FIG. 6, a beam of light emitted from a light source 101 such as a laser diode is collimated by a collimating lens 102 into a parallel beam of light, which is converted by a polarizer 103 into linearly polarized light vibrating in a vertical direction. The linearly polarized light passed through the polarizer 103 enters a liquid crystal element 104 where the polarization component in the direction of +45 degrees or −45 degrees relative to the vertical is phase-modulated. In the liquid crystal element 104, the long axes of the liquid crystal molecules are aligned in the direction of +45 degrees or −45 degrees (homogeneous alignment). The light passed through the liquid crystal element 104 emerges as elliptically polarized light, whose ellipticity varies with the voltage applied to the liquid crystal element 104.

The light passed through the liquid crystal element 104 is split by a half-silvered mirror 105 into reflected light and rectilinearly propagating light. The rectilinearly propagating light enters a quarter-wave plate 106 whose axis is oriented in the vertical axis direction, and the light is thus converted to linearly polarized light. At this time, since the polarization direction of the linearly polarized light depends on the ellipticity of the light passed through the liquid crystal element 104, the polarization direction varies depending on the voltage applied to the liquid crystal element 104. In this way, the polarization direction of the linearly polarized light can be modulated by the liquid crystal element 104. When the linearly polarized light whose polarization direction is thus modulated enters the test sample, the polarization direction is rotated by an unknown amount in accordance with the optical activity of the sample. The light passed through the sample enters a quarter-wave plate 108 where it is converted back to elliptically polarized light, and the elliptically polarized light enters an analyzer 109. Of the components of the incident light, only the component vibrating in the same direction as the transmission axis of the analyzer 109 is passed through the analyzer 109. The light passed through the analyzer 109 falls on a photodetector 110 where the light is converted into an electrical signal.

The reflected light separated by the half-silvered mirror 105 is not directed toward the sample but is directed to an analyzer 113. The light passed through the analyzer 113 falls on a photodetector 114 where the light is converted into an electrical signal.

The difference between the output signal of the photodetector 110 and the output signal of the photodetector 114 corresponds to the difference between the elliptically polarized light before entering the analyzer 109 and the elliptically polarized light before entering the analyzer 113 (that is, the angle of optical rotation through the sample). Accordingly, the angle of optical rotation through the sample can be measured from the difference between the output signal of the photodetector 110 and the output signal of the photodetector 114, and the concentration of component in the sample can be determined from the angle of optical rotation through the sample.

The signals output from the photodetectors 110 and 114 are transferred to a controller 123 via wiring lines 126 and 127. The controller 123 computes the angle of optical rotation based on the signals received from the photodetectors 110 and 114. By constantly receiving the signals, the optical rotation can be measured continuously. When it is detected that the optical rotation has reached a steady state, the concentration of a component is computed from the value of the optical rotation, the optical path length through the sample, and the value of the specific rotation of the optically active substance of interest, and the computed value is displayed on a display device 124. The controller 123 also has the function of driving the liquid crystal element 104 by creating a control signal based on the information received from the photodetector 114 and transmitting it via a wiring line 125 to the liquid crystal element 104.

The sample collected in a collection container 115 passes through a detector 122, a sampling valve 116, a pump 118, and an ion-exchange resin 117, and enters a sample cell 107. The sample cell 107 is constructed from a transparent pipe as shown, and a waste solution valve 121 is provided at the bottom of the cell. When performing the measurement, the valve 121 is closed to hold the sample in the cell, and when the measurement is completed, the valve 121 is opened to discharge the sample to the outside.

A regenerant pipe 120 equipped with a regenerant valve 119 is a mechanism necessary for regenerating the ion-exchange resin.

The detector 122 is a device for detecting the passage of the sample (for example, urine), and incorporates, for example, two electrodes configured so that whether or not the sample has passed therethrough can be determined by measuring the electrical resistance between the two electrodes.

In the optical measurement apparatus shown in FIG. 6, the flow rate of the pump 118 is set to 1 ml per second, and the capacity of the sample cell is set to 2 ml, while the capacity of the passage from the valve 116 to the sample cell is set to 3 ml.

Using the detection signal from the detector 122, the controller 123 measures the optical rotation by controlling the light source 101, the valve 116, the regenerant valve 119, the valve 121, and the pump 118 as will be described later.

Here, if the sample is urine and that the concentration of urine sugar is measured, when the substance to be removed is a negatively ionized amino acid ($H_2N$—CHR—$COO^-$), the reaction that occurs when removing the substance using a strong base anion-exchange resin is as shown by the following chemical equation (7).

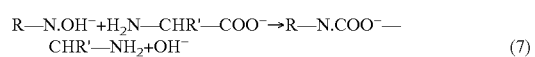

$$R\text{—}N.OH^- + H_2N\text{—}CHR'\text{—}COO^- \rightarrow R\text{—}N.COO^-\text{—}CHR'\text{—}NH_2 + OH^- \quad (7)$$

Here, R—N.OH⁻ represents the strong base anion-exchange resin, and R' designates the organic molecule unique to the amino acid.

Figure 7:
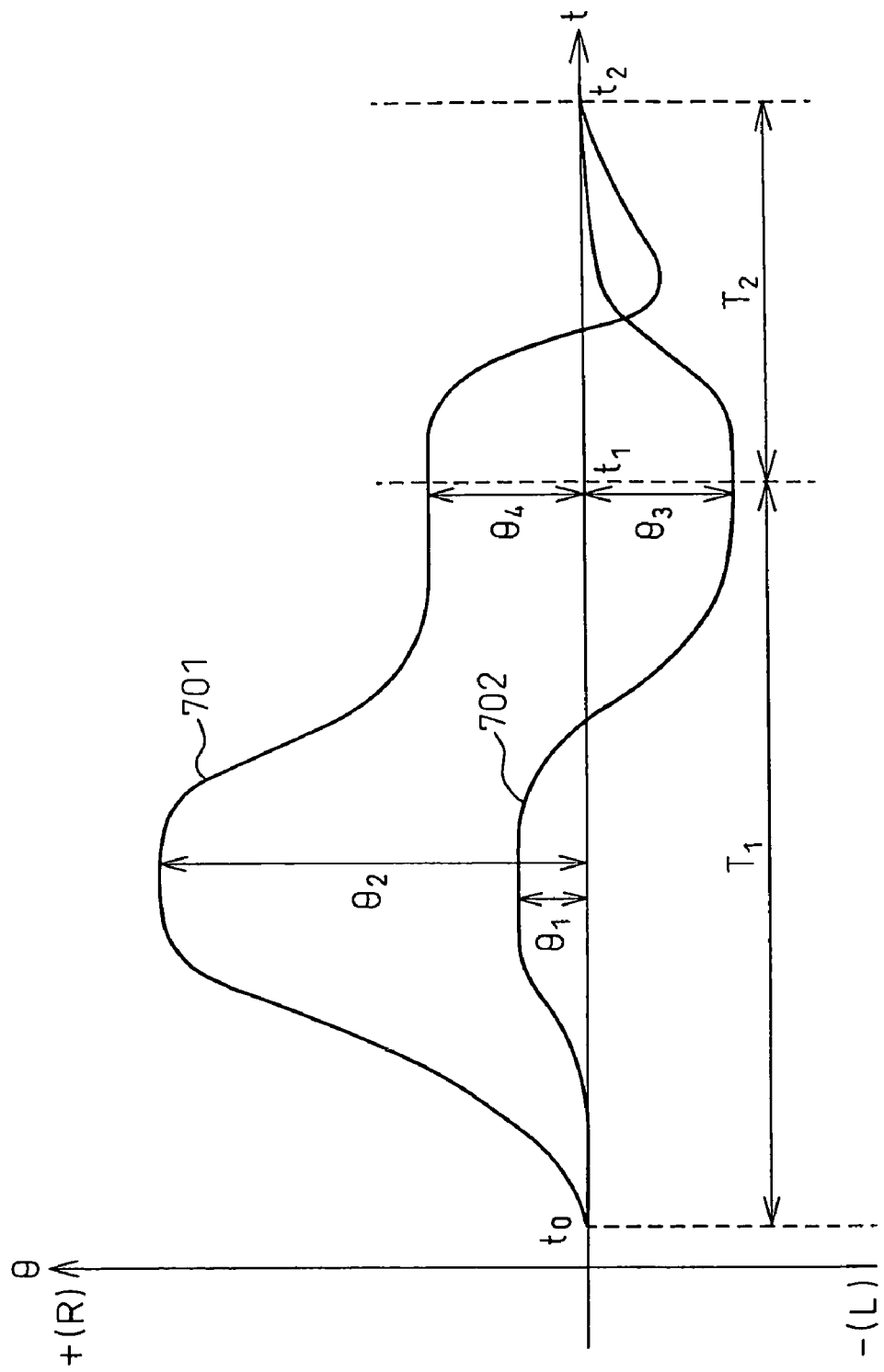
FIG. 7 is a graph showing the relationship between elapsed time and angle of optical rotation.

FIG. 7 shows the variation of the optical rotation angle θ (ordinate) as a function of elapsed time t (abscissa) when the optical rotation produced by urine sugar is continuously monitored.

In FIG. 7, graph 701 shows an example for the case of the urine of a diabetic patient, and graph 702 shows an example for the case of the urine of a healthy person. The feeding of the urine is started at time $t_0$ and ends at $t_1$, while the feeding of the regenerant is started at time $t_1$ and ends at $t_2$. That is, the urine feeding period is $T_1$ ($t_1-t_0$), and the regenerant feeding period is $T_2$ ($t_2-t_1$).

In FIG. 7, initially (at time $t_0$) the optical rotation is nearly zero, because the preservative solution filled into the ion-exchange resin flows into the sample cell. However, the influence of the preservative solution gradually diminishes, and a steady state is reached. The optical rotation $\theta_1$ or $\theta_2$ at this time represents the value after optically active components other than the urine sugar have been removed, that is, the value of the optical rotation produced by the urine sugar. If the concentration is calculated by detecting this optical rotation immediately after confirming the steady-state condition, the concentration can be determined with higher accuracy.

The relationship between the optical rotation (θ[deg]) and the concentration (c[g/dl]) is given by the following equation (8).

$$\theta = \tfrac{1}{100} \times \alpha_\lambda \times l \times c \tag{8}$$

where $\alpha_\lambda$ is the specific rotation of the optically active substance at wavelength λ, and l is the optical path length [dm] for measurement.

For example, when $\alpha_\lambda$ (glucose)=52.2 and l=1, then $\theta_1$=0.0104 in the case of a healthy person (urine sugar value: 0.02 g/dl) and $\theta_2$=0.416 in the case of a diabetic patient (urine sugar value: 0.8 g/dl).

When the optical rotation is continuously monitored after detecting $\theta_1$ or $\theta_2$, a great change occurs in the optical rotation being monitored. This is because the exchange ability of the ion-exchange resin gradually saturates finally reaching a point where ions of amino acids, etc. can no longer be adsorbed on the ion-exchange resin. Then, a steady state is again reached. The optical rotation $\theta_3$ or $\theta_4$ at this time can be interpreted as representing the optical rotation produced by the urine after the exchange ability of the ion-exchange resin has saturated, which is substantially the same as the optical rotation produced by the urine before it is passed through the ion-exchange resin. Accordingly, the optical rotation produced by amino acids, ascorbic acids, etc. can also be measured by the following equation (in the case of a healthy person).

[Optical rotation $\theta_3$ (optical rotation by urine)]=[Optical rotation $\theta_1$ (optical rotation by urine sugar)]+ [Optical rotation by optically active substances (amino acids, ascorbic acids, etc.) other than urine sugar]

Urine contains more than one kind of amino acid, and their properties and proportions differ. However, the proportion of the amount of amino acids contained in the urine to the total amount of urine is substantially constant for any person, and the specific rotation of each amino acid is known; therefore, if the specific rotation of the amino acids as a whole contained in the urine is assumed, the amino acid concentration can also be determined from the optical rotation obtained by the above equation.

Next, a measurement procedure for continuously measuring the optical rotation will be described.

The measurement procedure is performed by the controller 123 controlling the various elements shown in FIG. 6 in accordance with a prestored program.

(1) In the initial condition of the optical measurement apparatus shown in FIG. 6, the valves 116 and 119 are closed, the valve 121 is open, and the pump 118 is deactivated.

(2) Next, the controller 123 determines whether the user has pressed a measurement start button not shown.

(3) When the measurement start button is pressed, the controller 123 turns on the light source 101 and photodetectors 110 and 114 and drives the liquid crystal element 102.

(4) Then, the controller 123 determines whether the passage of urine is detected by the detector 122.

(5) When the passage of urine is detected by the detector 122, the controller 123 opens the valve 116, activates the pump 118, and continuously measures the optical rotation in the sample flowing through the sample cell 107 constructed from a transparent pipe. Data such as shown in FIG. 7 can be obtained by continuously measuring the optical rotation.

Figure 8:
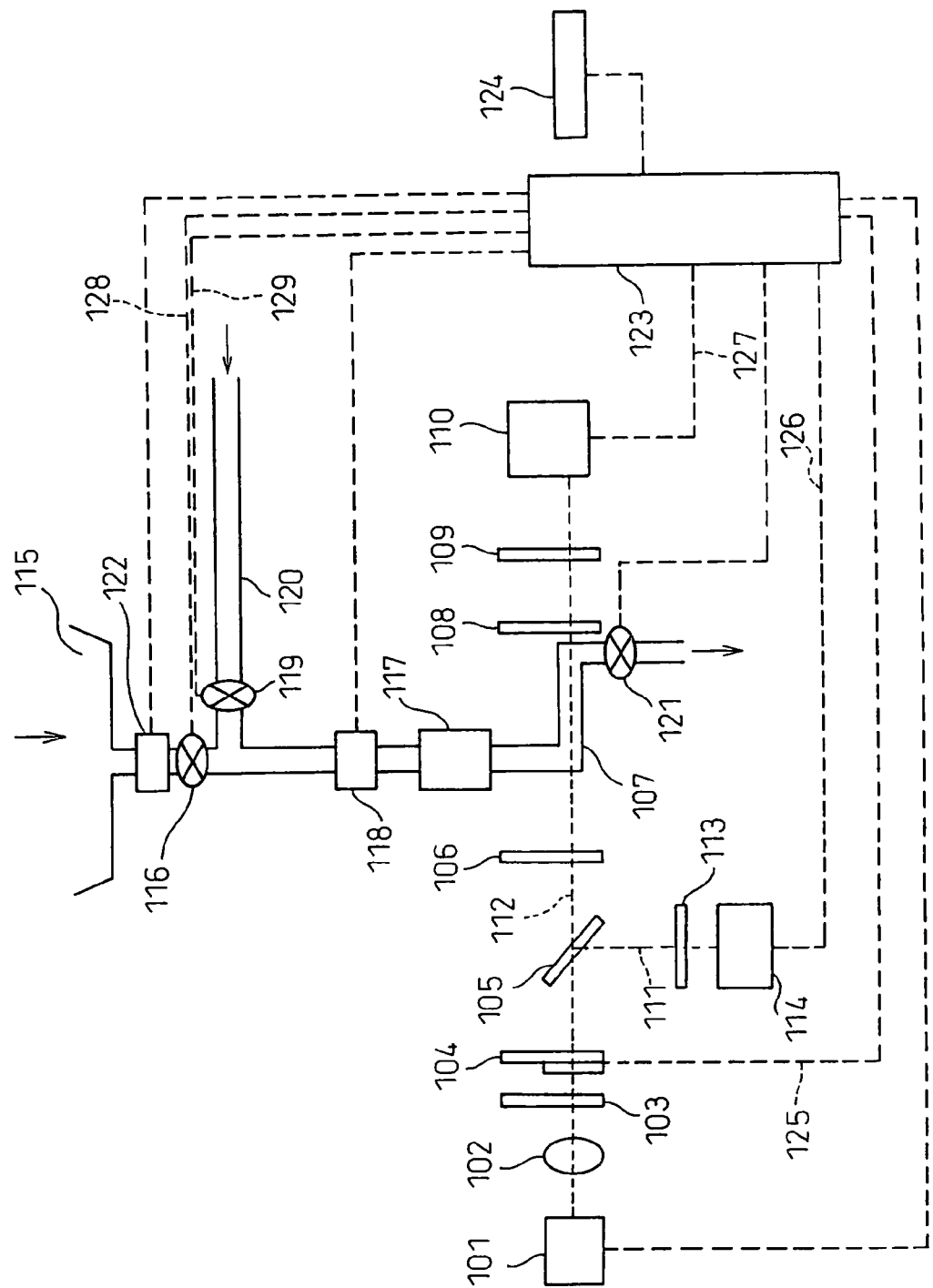
FIG. 8 is a diagram schematically showing the configuration of an optical measurement apparatus according to a seventh embodiment of the present invention.

FIG. 8 is a diagram schematically showing the configuration of an optical measurement apparatus according to a seventh embodiment of the present invention.

In FIG. 8, the system for measuring the optical rotation is the same as that of the sixth embodiment shown in FIG. 6. In the optical measurement apparatus shown in FIG. 8, when the controller 123 has finished measuring the concentration, information to that effect is sent to the sampling valve 116 via a wiring line 128. Upon receipt of this signal, the sampling valve 116, which was opened to feed the sample is closed. With this feedback control function, the amount of sample necessary for measurement can be controlled and managed.

When the exchange ability of the ion-exchange resin has saturated, the resin must be regenerated to restore it to a usable condition. The reaction that occurs when regenerating the strong base anion-exchange resin whose exchange ability has saturated due to adsorption of amino acids is as shown by the following chemical equation (9). Possible examples of the regenerant used here include alkaline ionized water and sodium hydroxide.

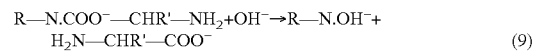

$$\text{R—N.COO}^-\text{—CHR'—NH}_2 + \text{OH}^- \rightarrow \text{R—N.OH}^- + \text{H}_2\text{N—CHR'—COO}^- \tag{9}$$

Here, R—N.OH⁻ represents the strong base anion-exchange resin, and R' designates the organic molecule unique to the amino acid.

While monitoring the optical rotation, when the second steady state is reached (at time t1 in FIG. 7) the regenerant is fed into the regenerant pipe 120 to gradually elute ions of amino acids, etc. adsorbed on the ion-exchange resin. When amino acids are being eluted, this means that the ion-exchange resin has not yet completely recovered its exchange ability. Further, the eluted solution exhibits some optical activity, because it contains amino acids. When the optical rotation becomes nearly zero (at time t2 in FIG. 7), this means that amino acids are no longer being eluted and, therefore, that the ion-exchange resin has recovered its exchange ability, that is, the regeneration is completed. When the completion of the regeneration is confirmed by the controller 123, information to that effect is sent to the regenerant valve 119 via a wiring line 129. Upon receipt of this signal, the regenerant valve 119, which was opened to feed the regenerant, is closed.

With this feedback control function, the amount of regenerant necessary for measurement can be controlled and managed.

Figure 9:
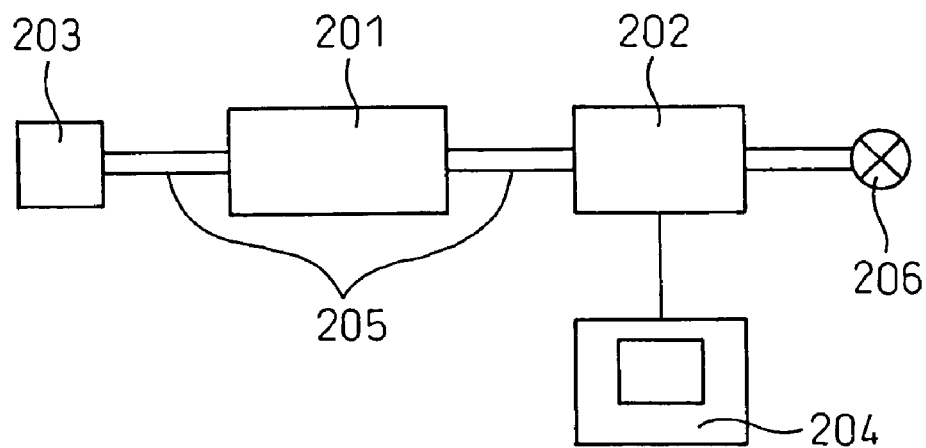
FIG. 9 is a diagram schematically showing the configuration of an optical measurement apparatus according to an eighth embodiment of the present invention.

FIG. 9 is a diagram schematically showing the configuration of an optical measurement apparatus according to an eighth embodiment of the present invention.

The measurement procedure for the optical measurement apparatus shown in FIG. 9 will be described with reference to FIG. 9. First, the sample is collected in a sample collection section 203. Next, the sample is introduced into an ion removal section 201 through a sample solution passage 205, and ions, as interfering substances, are removed. Next, the optical rotation in the sample is measured in a sensor section 202, and the concentration of a component is calculated and the result of the calculation displayed in a calculation/display section 204. Finally, a valve 206 is opened to discharge the sample to the outside.

Figure 10:
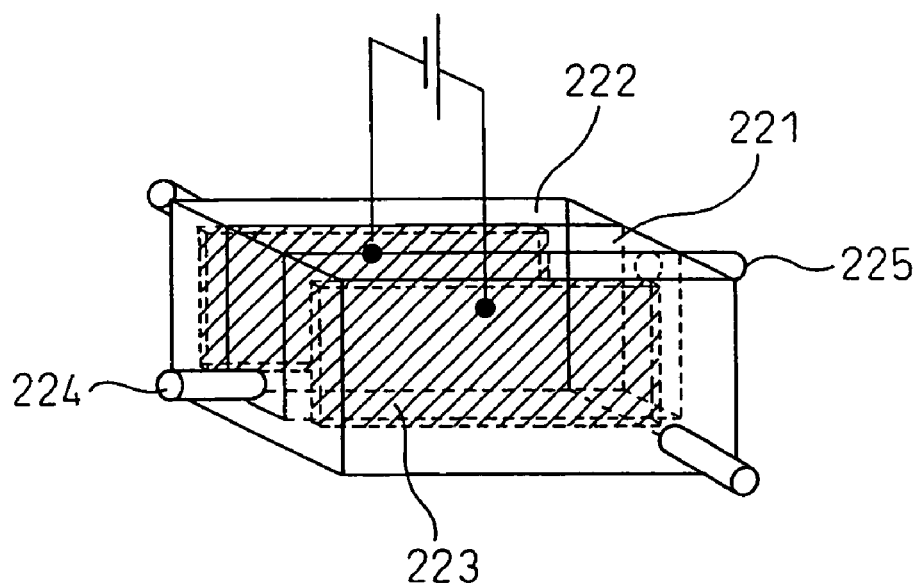
FIG. 10 is a perspective view of an ion removal section in the optical measurement apparatus according to the eighth embodiment of the present invention.
Figure 11:
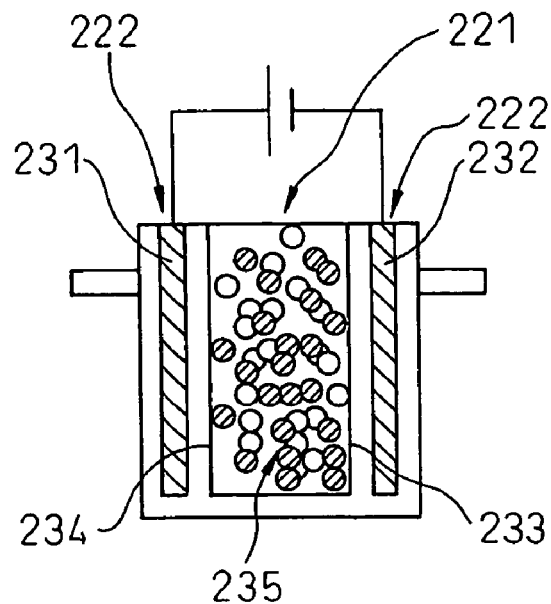
FIG. 11 is a cross-sectional view of the ion removal section in the optical measurement apparatus according to the eighth embodiment of the present invention.

FIGS. 10 and 11 show an example of the structure of the ion removal section 201 in the optical measurement apparatus shown in FIG. 9.

As shown in FIG. 10, the ion removal section comprises a sample chamber 221 and a waste solution chamber 222 enclosing the sample chamber 221 in a U-shaped form; the chambers are separated from each other by ion-exchange membranes. The sample chamber is filled with ion-exchange resins, and the waste solution chamber is provided with electrodes. The positional relationship between them will be described with reference to the cross-sectional view shown in FIG. 11. The sample chamber 221 is filled with ion-exchange resins 235. The waste solution chamber 222 has two regions, one on the left and the other on the right; the left-side region is provided with a positive electrode 231 and is separated from the sample chamber by an anion-exchange membrane 234. The right-side region is provided with a negative electrode 232 and is separated from the sample chamber by a cation-exchange membrane 233. Using a liquid feeding means such as a pump, the sample is fed into the sample chamber 221, and a waste solution is fed into the waste solution chamber 222. In FIG. 11, the protrusions on the left and right sides of the waste solution chamber are the inlet and outlet of the waste solution passage.

The sample is introduced through the sample chamber inlet 224 into the sample chamber 221, where ions are removed by the ion-exchange resins; thereafter, the sample is discharged through the sample chamber outlet 225 and directed to the sensor section. Using a mixed bed of anion-exchange and cation-exchange resins, both positive and negative ions can be removed by ion exchange.

At the same time, a voltage is constantly applied between the electrodes, causing the adsorbed ions to move under the influence of the applied electric field. On the negative electrode side, positive ions pass through the cation-exchange membrane 233 and move into the waste solution chamber 222, while on the positive electrode side, negative ions pass through the anion-exchange membrane 234 and move into the waste solution chamber 222. In this way, each ion-exchange resin is regenerated, preventing the ion-exchange ability from saturating. The removed ions are discharged with the waste solution.

Figure 12:
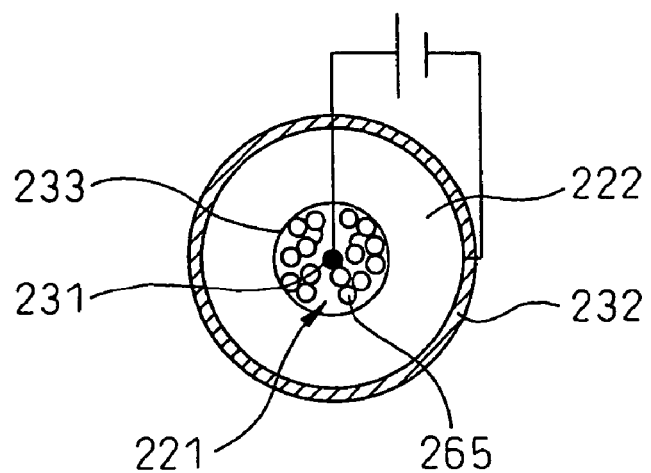
FIG. 12 is a cross-sectional view of an ion removal section in an optical measurement apparatus according to a ninth embodiment of the present invention.
Figure 13:
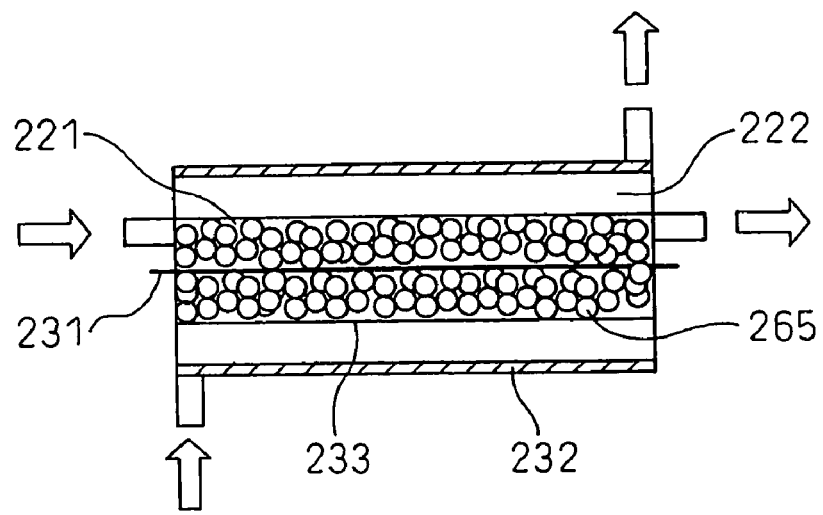
FIG. 13 is a cross-sectional view of the ion removal section in the optical measurement apparatus according to the ninth embodiment of the present invention.

FIGS. 12 and 13 are diagrams schematically showing the configuration of an optical measurement apparatus according to a ninth embodiment of the present invention.

In the present embodiment, the configuration, other than the ion removal section, is the same as that of the eighth embodiment shown in FIGS. 9 to 11; therefore, only the ion removal section will be described with reference to FIGS. 12 and 13. FIGS. 12 and 13 respectively show cross-sectional views of the ion removal section taken in mutually perpendicular directions.

As shown in FIG. 12, the sample chamber 221 and the waste solution chamber 222 are arranged in concentric fashion and separated from each other by a cation-exchange membrane 233. A positive electrode 231 is provided in the center, and a cylindrically shaped negative electrode 232 is provided around the outer circumference. The sample chamber 221 is filled with a cation-exchange resin 265. Using a liquid feeding means, the sample is fed into and discharged from the sample chamber 221, and the waste solution is fed into and discharged from the waste solution chamber 222.

When a voltage is applied between the electrodes while feeding the sample, a reaction such as represented by $2H_2O \rightarrow 4H^+ + 4e^-$ occurs at the positive electrode disposed in the sample chamber, and the pH moves into the acid range. With this reaction, many of substances that contain functional groups are ionized into positive ions and, with substances that are originally positive ions, are adsorbed onto the cation-exchange resin 265 filled into the sample chamber. Accordingly, by passing the sample through the sample chamber, many of interfering substances can be removed. Therefore, if the sample from which such interfering substances have been removed is sent to the sensor section to measure the optical rotation, the concentration of the substance of interest can be measured by eliminating the effects of the interfering substances contained in the sample.

Further, under the influence of the applied electric field, the adsorbed positive ions move through the ion-exchange resin toward the outer circumference, and finally pass through the cation-exchange membrane 233 and enter the waste solution chamber 222, thus accomplishing the regeneration of the ion-exchange resin. By constantly applying the electric field, the ion-exchange resin can be maintained in a regenerated condition, so that when the sample is fed, ions in the sample can be quickly removed by adsorption.

The above example has been described for the case of a cation-exchange resin, but an anion-exchange resin can also be used in the above structure. In that case, however, the negative electrode is provided in the center, and the positive electrode, which in this case is cylindrical in shape, is provided around the outer circumference; further, an anion-exchange membrane is provided to separate the sample chamber from the waste solution chamber, and the sample chamber is filled with an anion-exchange resin. In this case, when the voltage is applied, as the pH in the sample chamber moves into the alkaline range, many of the substances that contain functional groups turn into negative ions and are thus adsorbed onto the anion-exchange resin for removal.

When measuring the concentration of glucose in urine, amino acids in the urine are the interfering substances. Various kinds of amino acids are contained in the urine but, by turning them into positive or negative ions depending on the kind of the amino acid, they can be easily removed by adsorption.

The urine sample has a pH of weak acidity. For example, in the case of basic amino acids such as histidine (isoelectric point: 7.59), if the amino acids are ionized into positive ions by adjusting the pH so as to make the sample acid, the amino acids can be easily removed by adsorption, because the adjusting range of the pH is smaller than when ionizing them into negative ions. In this case, it is preferable to use a cation-exchange resin for adsorption and removal.

On the other hand, in the case of cystine (isoelectric point: 4.60) or serine (isoelectric point: 5.68), it is preferable to ionize them into negative ions by adjusting the pH so as to make the sample alkaline, and to adsorb and remove them using an anion-exchange resin. For example, consider an amino acid solution of histidine and serine; in this case, when the solution is made acid by adjusting the pH to 3 and is fed to a commercially available conventional strong acid anion-exchange resin (10 ml) at a rate of about 25 ml/min., histidine can be adsorbed and removed 100%, but in the case of serine, only 50% can be removed. Furthermore, the urine contains various kinds of amino acids of different isoelectric points; therefore, if the amino acids as interfering substances are to be removed quickly and reliably, it is desirable that the sample be processed using two structures arranged in series.

Figure 14:
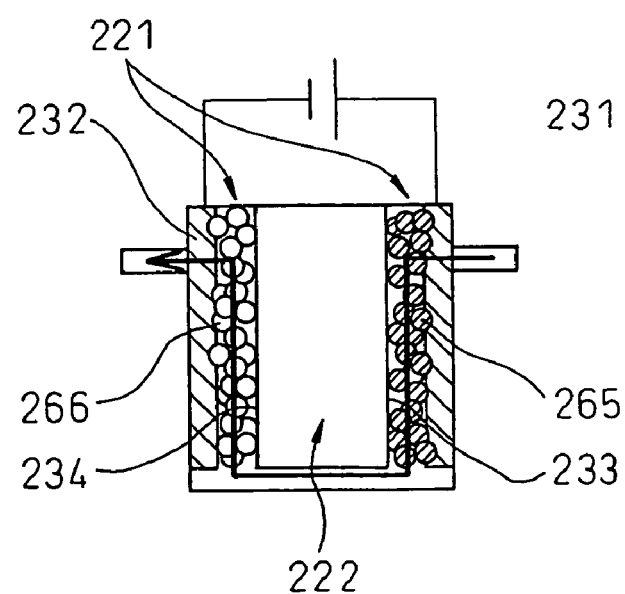
FIG. 14 is a cross-sectional view of an ion removal section in an optical measurement apparatus according to a 10th embodiment of the present invention.

FIG. 14 is a diagram schematically showing the configuration of an optical measurement apparatus according to a 10th embodiment of the present invention.

In the present embodiment, the configuration other than the ion removal section is the same as that of the eighth embodiment shown in FIGS. 9 to 11; therefore, only the ion removal section will be described with reference to FIG. 14.

FIG. 14 is a cross-sectional view showing the ion removal section; as can be seen, the positional relationship between the sample chamber and the waste solution chamber is reversed from that in the eighth embodiment. Functionally, the configuration is the same as when the anion-exchange and cation-exchange resins are arranged in series. The sample flows through a U-shaped channel as indicated by an arrow in the FIGURE. It is desirable that the channel connecting between the two anion and cation sample chambers be designed so as to optimize the sample flow in each sample chamber. It is also desirable that a mesh-like filter be installed in the channel connecting between the sample chambers in order to prevent the anion-exchange and cation-exchange resins from mixing together. The sample fed to the sample chamber 221 is first introduced into the positive electrode side where the pH is adjusted to make the solution acid so that the ions are adsorbed onto the cation-exchange resin 265. Next, the sample is directed into the negative electrode side where the pH is adjusted to make the solution alkaline so that the ions are adsorbed onto the anion-exchange resin 266. In this way, both the positive and negative ions can be removed.

Here, an electric field is applied between the positive electrode 231 and the negative electrode 232; therefore, the positive ions adsorbed on the cation-exchange resin 265 and the negative ions adsorbed on the anion-exchange resin 266 are both subjected to a force toward the waste solution chamber 222 located in the center. As a result, the positive ions and the negative ions pass through the cation-exchange membrane 233 and the anion-exchange membrane 234, respectively, and enter the waste solution chamber 222. This accomplishes the regeneration of the ion-exchange resins.

The effect of the voltage application will be described below by taking as an example the case where an amino acid-containing physiological saline solution was used as the sample.

Figure 15:
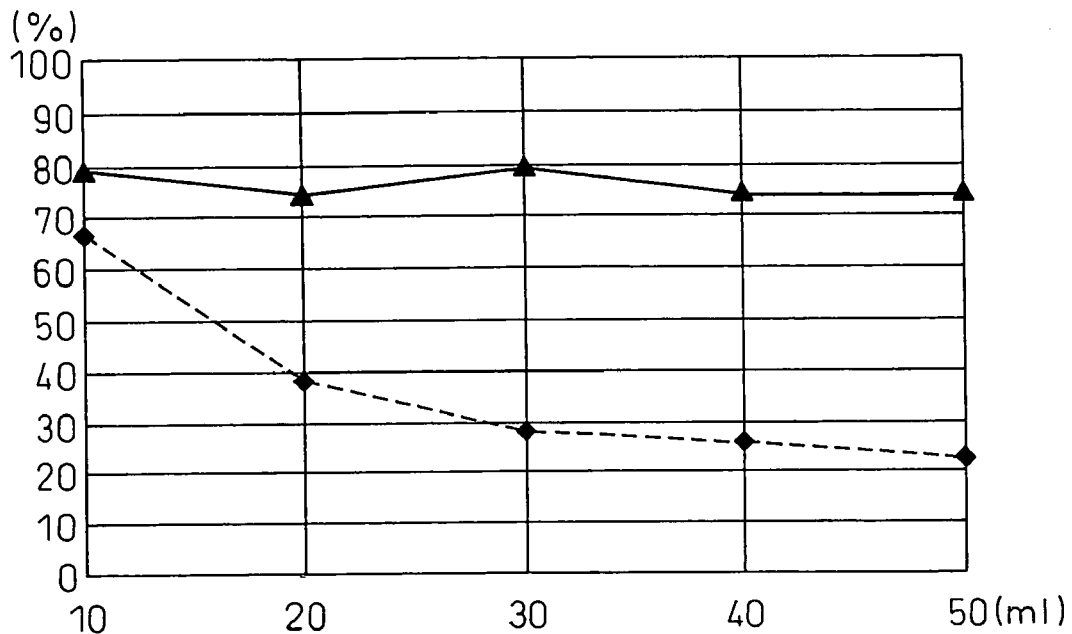
FIG. 15 is a graph showing the effect of voltage application in the optical measurement apparatus according to the 10th embodiment of the present invention.

FIG. 15 shows the results of the experiment conducted with a sample prepared by dissolving histidine in a physiological saline solution at a concentration of 300 mg/dl.

In FIG. 15, the abscissa represents the feed amount of the solution (ml) and the ordinate represents the removal ratio (%). In the absence of an applied voltage, the removal ratio of the amino acid (histidine) decreases as the feed amount of the sample increases. On the other hand, in the presence of an applied voltage, the initial value of the removal ratio is high and, besides, the removal ratio does not decrease. Here, the absolute value of the removal ratio in the presence of an applied voltage is at about 80%, because the amount of the ion-exchange resin was reduced in order to check the effect of the voltage application, but it should be understood that if the amount of the ion-exchange resin is sufficient, or if the feed rate of the solution is reduced, a removal ratio close to 100% can be achieved.

With the ion removal section having the above structure, the adjustment of the pH to make the solution acid or alkaline, the removal of positive and negative ions by adsorption, and the regeneration of the anion-exchange and cation-exchange resins can be done at the same time by using a pair of electrodes. A sample with ions removed, by passing through the ion removal section, is sent to the sensor section to measure the optical rotation from which the concentration of the substance of interest, for example, glucose, can be obtained.

Figure 16:
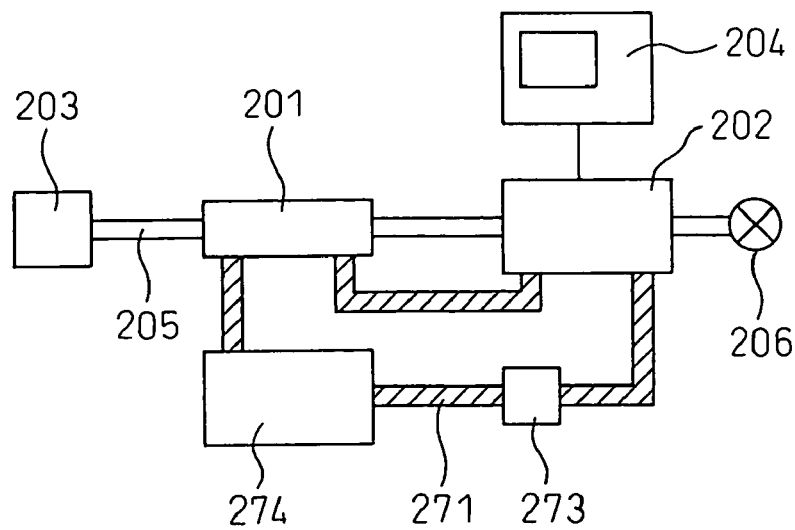
FIG. 16 is a diagram schematically showing the configuration of an optical measurement apparatus according to an 11th embodiment of the present invention.

FIG. 16 is a diagram schematically showing the configuration of an optical measurement apparatus according to an 11th embodiment of the present invention.

The basic configuration of the optical measurement apparatus of this embodiment is the same as that of the eighth to tenth embodiments described above. In FIG. 16, the sample collected in the sample collection section 203 is introduced into the ion removal section 201 through the sample solution passage 205. The sample from which the ions of the interfering substances have been removed is sent to the sensor section 202 where the optical rotation is measured, from which the concentration of component is computed. In the ion removal section 201, a temperature control solution used to control the temperature of the sensor section is utilized as the waste solution into which the adsorbed ions are discharged. The temperature control solution is controlled to a constant temperature in a thermostatic bath 274 and is circulated by a pump 273 through a temperature control solution passage 271 indicated by oblique hatching in the FIGURE. When the component is urine sugar, a high measurement accuracy is required of the sensor because the sugar concentration level to be measured is very low. As any temperature variation in the sensor section can lead to a degradation of the measurement accuracy, the temperature of the sensor section must be controlled in order to maintain the high measurement accuracy. Further, as the temperature of the urine is almost the same as the body temperature of the subject, the sensor section must be controlled to a temperature near the body temperature. It should also be noted that the body temperature can vary from person to person and from hour to hour in the day and, therefore, by just introducing the urine as the sample into the sensor section, a temperature variation may occur leading to a degradation of the measurement accuracy.

Here, when the temperature control solution is utilized as the waste solution, and as the sample is in contact with the waste solution through an ion-exchange membrane, heat exchange occurs between them to reduce the temperature difference between the sample and the waste solution. Accordingly, when such a sample is fed into the ion removal section, not only are the interfering substances removed there, but also the temperature difference between the sample and the sensor section 202 is reduced. That is, by feeding the sample into the sensor section 202, the temperature difference between the sample and the sensor section 202 can be eliminated, achieving a highly accurate and stable measurement.

Figure 17:
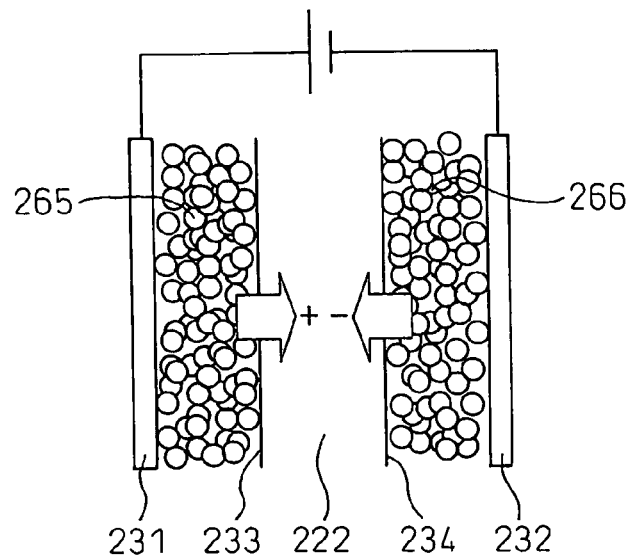
FIG. 17 is a diagram for explaining the principle of continuous ion-exchange EDI.

FIG. 17 is a diagram for explaining a continuous ion-exchange EDI (Electronic De-Ionization) system.

The principle behind the movement of positive and negative ions shown in the eighth to 11th embodiments above will be explained with reference to FIG. 17.

In the structure of FIG. 17, if a voltage such as shown in the FIGURE is applied, on the positive electrode 231 side, the positive ions adsorbed on the cation-exchange resin 265 move under the influence of the applied electric field, and pass through the cation-exchange membrane 233 and enter the waste solution chamber 222. Similarly, on the negative electrode 232 side, the negative ions adsorbed on the anion-exchange resin 266 move under the influence of the applied electric field, and pass through the anion-exchange membrane 234 and enter the waste solution chamber 222. Such a system is called a continuous ion-exchange EDI system, and has found commercial implementation in pure water production apparatuses, etc.

Figure 18:
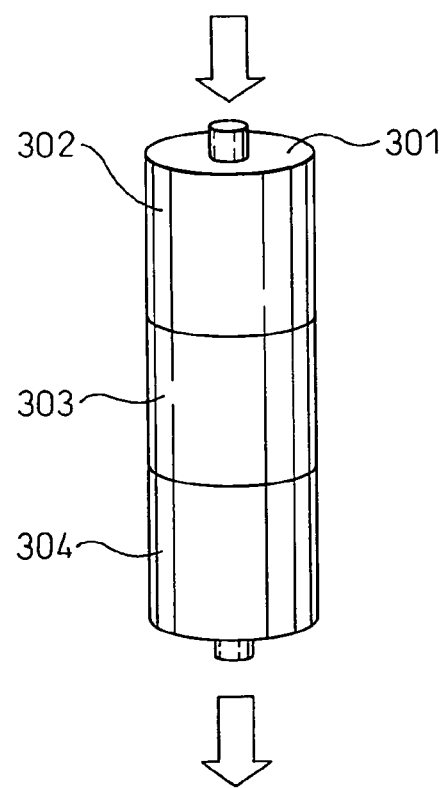
FIG. 18 is a diagram showing one example of an ion-exchange resin cartridge.

FIG. 18 is a diagram showing an ion-exchange resin cartridge.

The ion-exchange resin cartridge 301 shown in FIG. 18 can be used in place of the ion-exchange resin section 3 in the first to fifth embodiments or the ion-exchange resin 117 in the sixth and seventh embodiments.

The ion-exchange resin cartridge 301 comprises a charcoal filter layer 302, a synthetic adsorbent layer 303, and an ion-exchange resin section 304. In the FIGURE, the urine sample is passed through the ion-exchange resin cartridge 301 in the direction indicated by an arrow. The charcoal filter layer 302 mainly removes color components from the urine, and the synthetic adsorbent layer 303 mainly removes lipid components from the urine, while the ion-exchange resin section 304 removes amino acids and ascorbic acid, as previously described.

As it is provided with the charcoal filter layer 302 and the synthetic adsorbent layer 303 in addition to the ion-exchange resin section 304, the ion-exchange resin cartridge 301 can remove interfering substances other than the optically active component from the urine with higher efficiency, and thus the measurement accuracy can be further enhanced.

As the component which can be adsorbed differs depending on the pore diameter of the synthetic adsorbent in the synthetic adsorbent layer 303, it is preferable to use synthetic adsorbents having different pore diameters. It is also preferable to optimize the capacity of each layer by considering the components of the urine so that each layer can perform its function as effectively as possible.

Here, the synthetic adsorbent, unlike the ion-exchange resin, does not have functional groups, but has a surface area comparable to that of activated carbon, and continuous pores called micropores are formed extending deep inside the particles. Accordingly, the synthetic adsorbent can efficiently adsorb organic substances contained in an aqueous solution.

Figure 19:
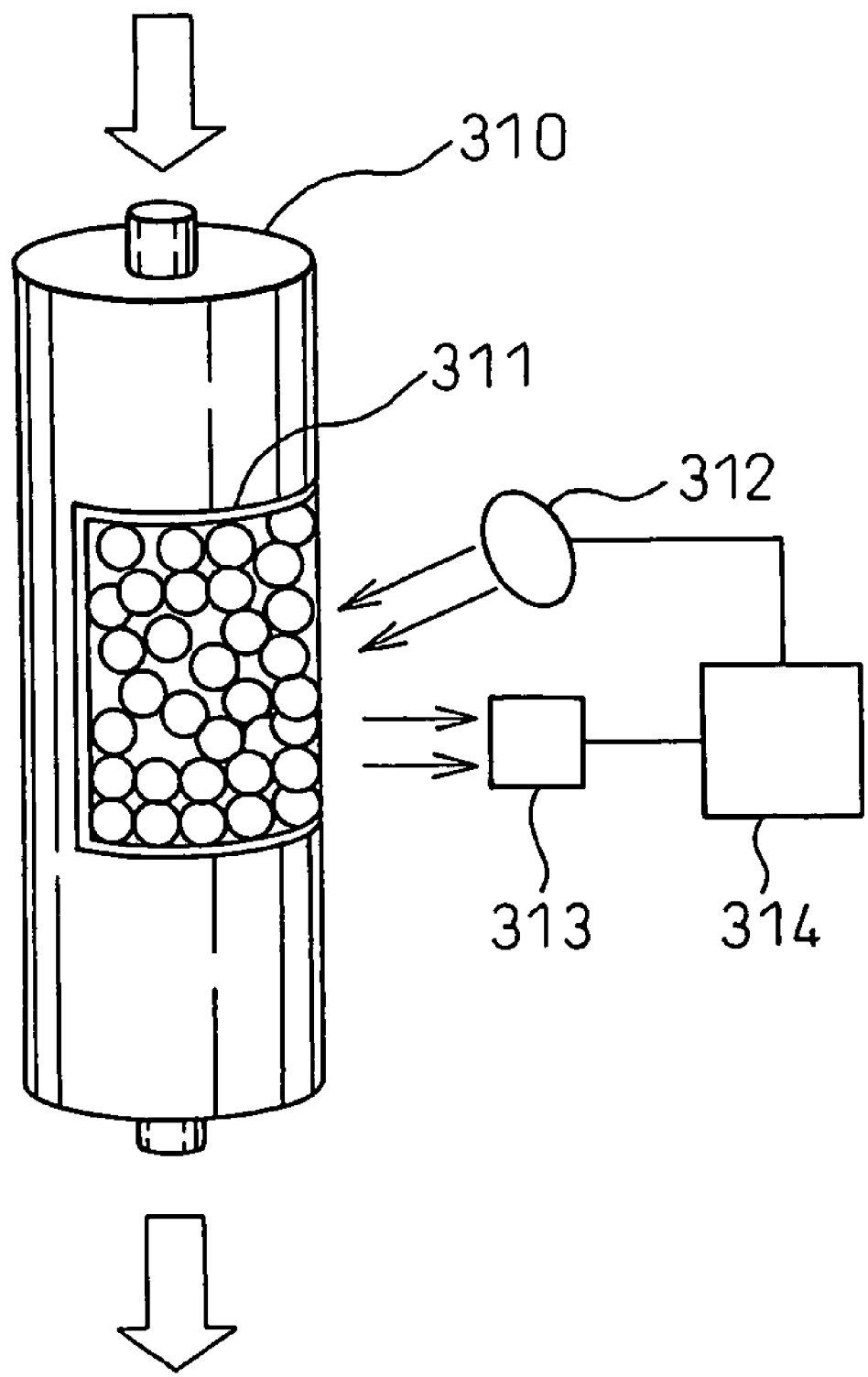
FIG. 19 is a diagram showing another example of the ion-exchange resin cartridge.

FIG. 19 is a diagram showing another ion-exchange resin cartridge.

The ion-exchange resin cartridge 310 shown in FIG. 19 can be used in place of the ion-exchange resin section 3 in the first to fifth embodiments or the ion-exchange resin 117 in the sixth and seventh embodiments.

In the ion-exchange resin cartridge 310, the column filled with the ion-exchange resin has a window 311 formed from a transparent resin or the like. Therefore, the condition of the ion-exchange resin can be observed from the outside through the window 311. For example, if a resin is used that changes color when its ion-exchange ability drops or is lost, then whether the ion-exchange resin cartridge 310 needs replacing or not can be easily determined by visually checking the condition through the window 311.

Further, an ion-exchange resin color checking device can be constructed using, for example, a light-emitting device 312 for illuminating the ion-exchange resin through the window 311, a photodetector 313 which receives reflected light from the ion-exchange resin, and a controller 314 (PC, CPU, etc.) which receives a detection signal from the photodetector 313. In such a color checking device, the light-emitting device 312 is flashed at suitable intervals of time or once in every predetermined number of measurements, and the color of the ion-exchange resin is checked based on the detection signal from the photodetector 313; then, when it is determined that the ion-exchange resin needs replacing, the user can be automatically notified. Here, the color of the ion-exchange resin can be checked, for example, by analyzing the spectrum of the light received by the photodetector 313 using a sensor in the photodetector section, and by measuring the reflectivity at each wavelength.

Figure 20:
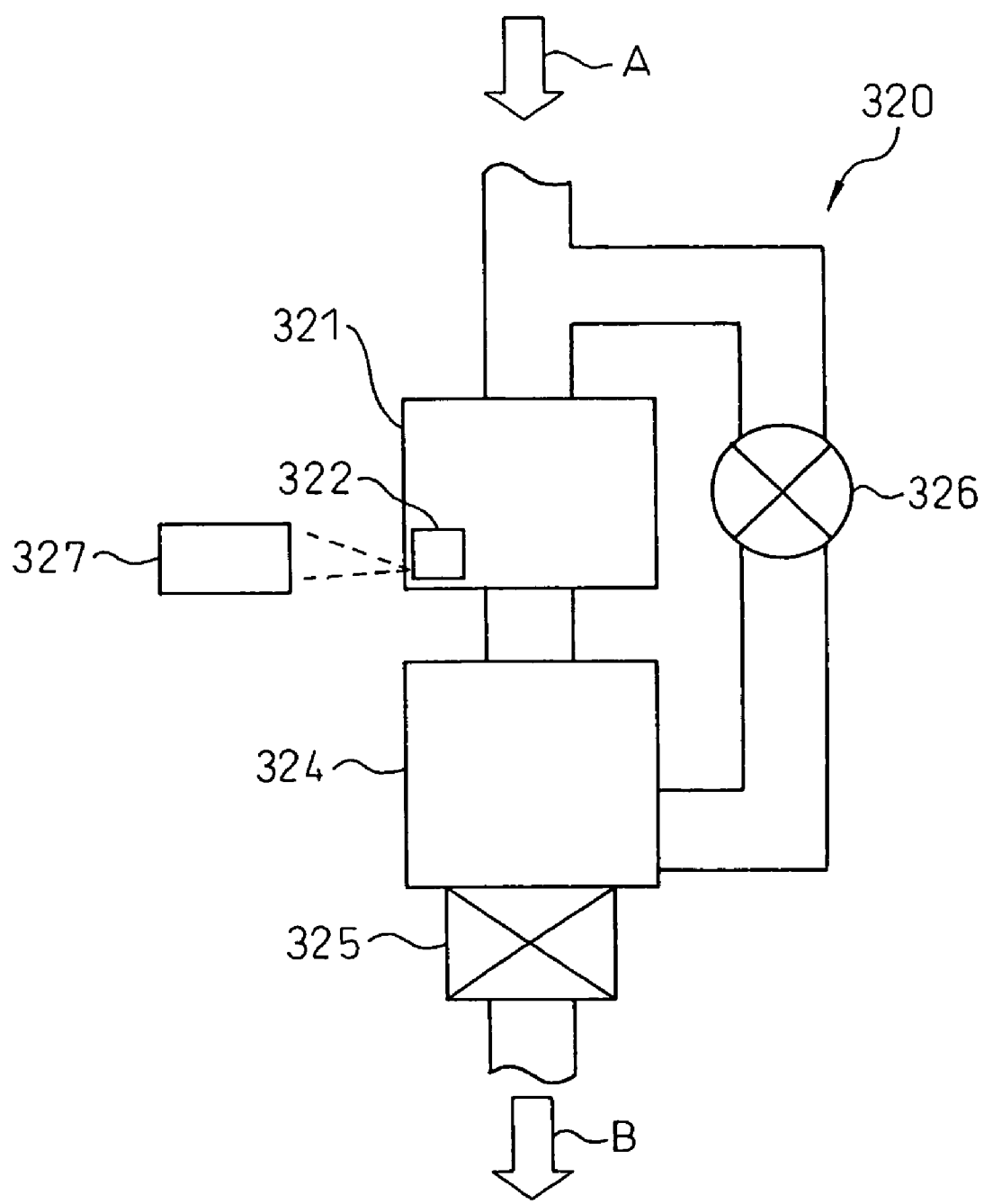
FIG. 20 is a diagram showing one example of an ion-exchange resin cartridge structure.

FIG. 20 is a diagram showing an ion-exchange resin cartridge structure.

The ion-exchange resin cartridge structure 320 shown in FIG. 20 can be used in place of the ion-exchange resin section 3 in the first to fifth embodiments or the ion-exchange resin 117 in the sixth and seventh embodiments.

The ion-exchange resin cartridge structure 320 comprises a column 321 filled with an ion-exchange resin, a sample holding cell 324, a valve 325, and a circulating pump 326. The column 321 has a window 322 through which to observe the ion-exchange resin filled therein. Further, the ion-exchange resin color checking device 327 described with reference to FIG. 19 is disposed near the window 322.

When the urine sample is introduced into the ion-exchange resin cartridge structure 320 as shown by an arrow A, the sample passes through the column 321. At this time, the valve 325 is closed, and the sample is temporarily held in the sample holding cell 324. Next, the color of the ion-exchange resin contained in the column is checked through the window 322 by using the ion-exchange resin color checking device described with reference to FIG. 19.

From the color of the ion-exchange resin through which the sample has passed, it can be determined whether the interfering substances have been sufficiently removed from the sample. That is, if the color of the ion-exchange resin has changed when it is observed after the sample has passed through it, it can be determined that the exchange ability has saturated and therefore that the interfering substances have not been sufficiently removed from the sample.

If it is determined from the resin color that the ion-exchange resin has performed well (that is, the interfering substances have been sufficiently removed from the sample), the valve 325 is opened, and the sample is sent, for example, to the measurement container 55 (arrow B).

On the other hand, if it is determined from the resin color that the ion-exchange resin has not performed well (that is, the interfering substances have not been sufficiently removed from the sample), the user is instructed to replace the column or regenerate the ion-exchange resin contained in the column. After replacing the column or regenerating the ion-exchange resin contained in the column, the pump 326 is activated to feed the sample from the sample holding cell 324 into the column 321.

If the sample is a biological sample, the amount of interfering components contained in the biological sample varies from person to person and, therefore, the amount of ion-exchange resin necessary for removing the interfering components also differs. When the ion-exchange resin cartridge structure 320 shown in FIG. 20 is used, it becomes possible to prevent a measurement from being made without sufficiently removing the interfering components.

Figure 21:
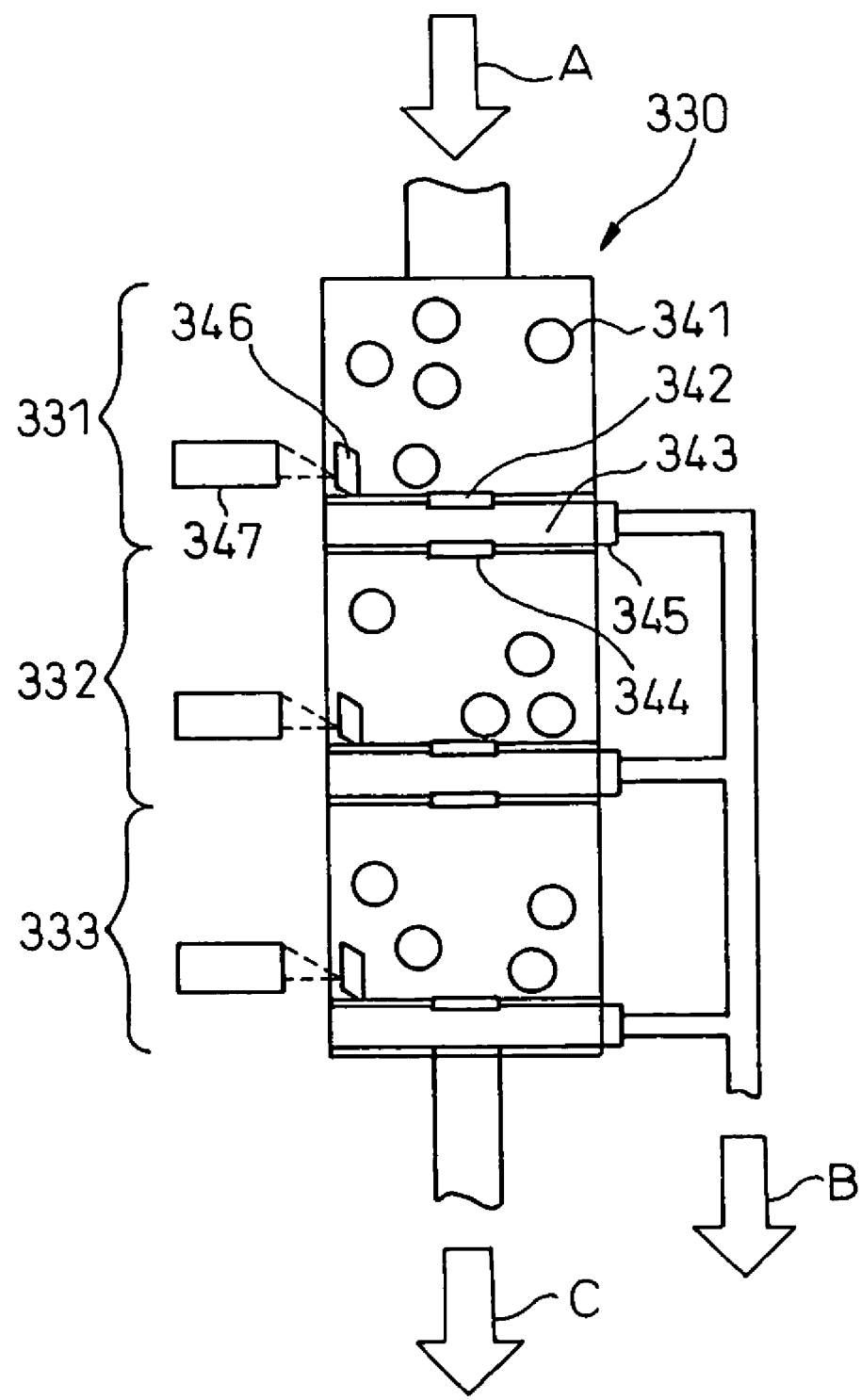
FIG. 21 is a diagram showing another example of the ion-exchange resin cartridge structure.

FIG. 21 is a diagram showing another ion-exchange resin cartridge structure.

The ion-exchange resin cartridge structure 330 shown in FIG. 21 can be used in place of the ion-exchange resin section 3 in the first to fifth embodiments or the ion-exchange resin 117 in the sixth and seventh embodiments.

The ion-exchange resin cartridge structure 330 comprises a plurality of blocks 331 to 333. In the example of FIG. 21, the ion-exchange resin cartridge structure 330 is made up of three blocks, but more than three blocks may be used.

Each block includes an ion-exchange resin section 341, a resin leakage preventing filter 342, a sample holding cell 343, a first valve 344, a second valve 345, and a window 346. Further, the ion-exchange resin color checking device 347 described with reference to FIG. 19 is disposed near each window 346. In each block, the first valve, the second valve, and the color checking device are controlled by a controller in accordance with a prescribed program.

When the urine sample is introduced into the ion-exchange resin cartridge structure 330 as shown by an arrow A, the sample passes through the ion-exchange resin section 341 of the first block 331. At this time, the first and second valves 344 and 345 are closed, and the sample is temporarily held in the sample holding cell 343. Next, the color of the ion-exchange resin section 341 is checked through the window 346 by using the ion-exchange resin color checking device described with reference to FIG. 19.

As described above, from the color of the ion-exchange resin through which the sample has passed, it can be determined whether the interfering substances have been sufficiently removed from the sample. That is, if the color of the ion-exchange resin has changed when it is observed after the sample has passed through it, it can be determined that the exchange ability has saturated and therefore that the interfering substances have not been sufficiently removed from the sample.

If it is determined from the resin color that the ion-exchange resin has performed well (that is, the interfering substances have been sufficiently removed from the sample), the second valve 345 is opened, and the sample is sent, for example, to the measurement container 55 (arrow B).

On the other hand, if it is determined from the resin color that the ion-exchange resin has not performed well (that is, the interfering substances have not been sufficiently removed from the sample), the first valve 344 is opened, and the sample is sent to the second block 332. Thereafter, the same operation as described above is repeated, and the sample passed through the block whose ion-exchange resin layer has been determined as performing well is sent to the measurement container 55 (arrow B). If it is determined that the ion-exchange resin layer in every one of the blocks has failed to perform well, the sample is discarded (arrow C).

If the sample is a biological sample, the amount of interfering components contained in the biological sample varies from person to person and, therefore, the amount of ion-exchange resin necessary for removing the interfering components also differs. When the structure shown in FIG. 21 is used, the resin can be checked to see if its exchange ability has saturated, each time the sample is passed through the layer formed from a small amount of ion-exchange resin; in this way, the sample can be passed through an amount of resin that is just sufficient to remove the interfering components contained in the sample. As the sample can be prevented from passing through more than the necessary amount of ion-exchange resin, the amount of variation of the concentration of a component can be reduced.

Figure 22:
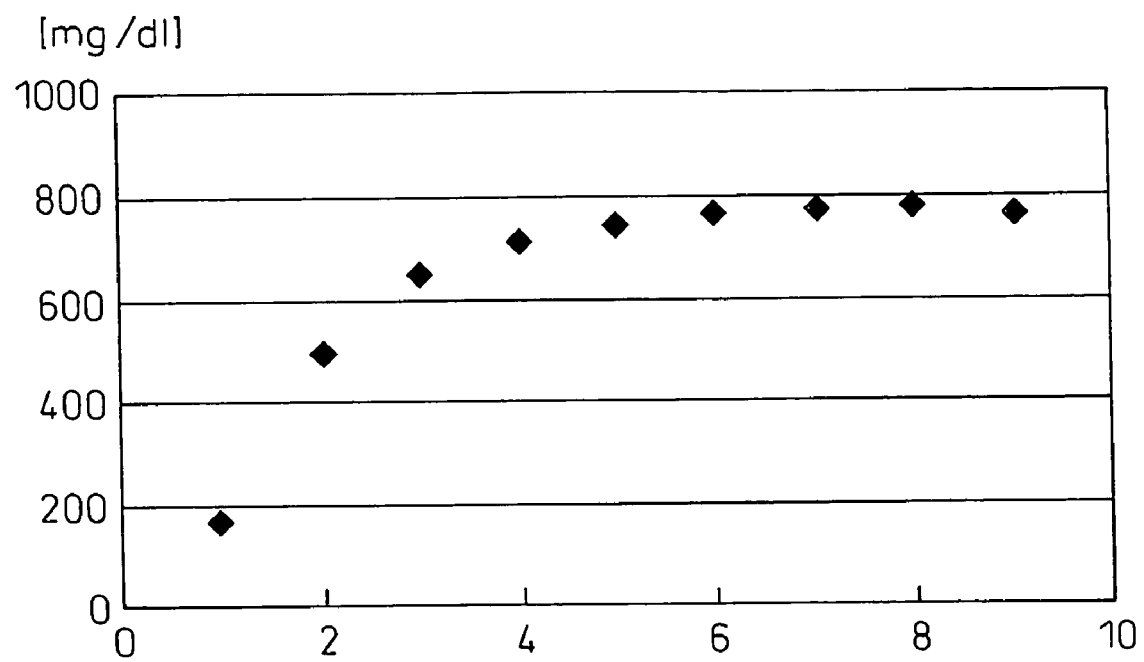
FIG. 22 is a diagram showing the concentration of glucose in a sample passed through a column.

FIG. 22 is a diagram showing the concentration of glucose in the sample passed through the column.

The diagram of FIG. 22 shows the results obtained by feeding a sample containing a prescribed amount of glucose into a fresh column 117, 1 ml at a time, and by measuring the glucose concentration in the sample passed through the column. In FIG. 22, the ordinate represents the glucose concentration in the sample, and the abscissa represents the number of times that the sample was passed through the column 117 in the optical measurement apparatus shown in FIG. 6.

As shown in FIG. 22, the measurement results from the sixth measurement onward show substantially the same value. As a fresh column contains a preservative solution, moisture, etc., an accurate measurement result may not be obtained from the sample that first passes through the column. Therefore, in the earlier described example, the measurement was made continuously as shown in FIGS. 6 and 7, and the value obtained when the measurement result settled to a steady-state value was taken as the measurement value. This method, however, takes time and labor to make the measurement. In view of this, if the number of times the sample should be passed through the column before an accurate measurement can be made is determined in advance, and the measurement is made after passing the sample through the column the predetermined number of times, then an accurate measurement value can be obtained in a single measuring operation.

A measurement procedure for measuring the optical rotation in a single measuring operation will be described below.

The measurement procedure is performed by the controller 123 controlling the various elements shown in FIG. 6 in accordance with a prestored program. Here, it is assumed that, once 2 ml of a sample is passed through the fresh column 117, an accurate measurement can thereafter be made. It is also assumed that three seconds after the sample is introduced into the system, the sample begins to enter the sample cell 107, that five seconds after the introduction, the sample cell 107 is filled with the sample, and that seven seconds after the introduction, the first 2 ml of sample is drained from the sample cell 107.

(1) In the initial condition of the optical measurement apparatus shown in FIG. 6, the valves 116 and 119 are closed, the valve 121 is open, and the pump 118 is deactivated.

(2) Next, the controller 123 determines whether the user has pressed a measurement start button not shown.

(3) When the measurement start button is pressed, the controller 123 turns on the light source 101 and photodetectors 110 and 114 and drives the liquid crystal element 102.

(4) Then, the controller 123 determines whether the passage of urine is detected by the detector 122.

(5) When the passage of urine is detected by the detector 122, the controller 123 opens the valve 116 and activates the pump 118.

(6) When seven seconds have elapsed after the passage of urine was detected by the detector 122, the controller 123 closes the valve 121 and measures the optical rotation in the sample held in the sample cell 107 constructed from a transparent pipe. As the first 2 ml of sample introduced into the column 117 has drained from the system when seven seconds have elapsed after the passage of urine was detected by the detector 122, as described above, the measurement can be made accurately.

Figure 23:
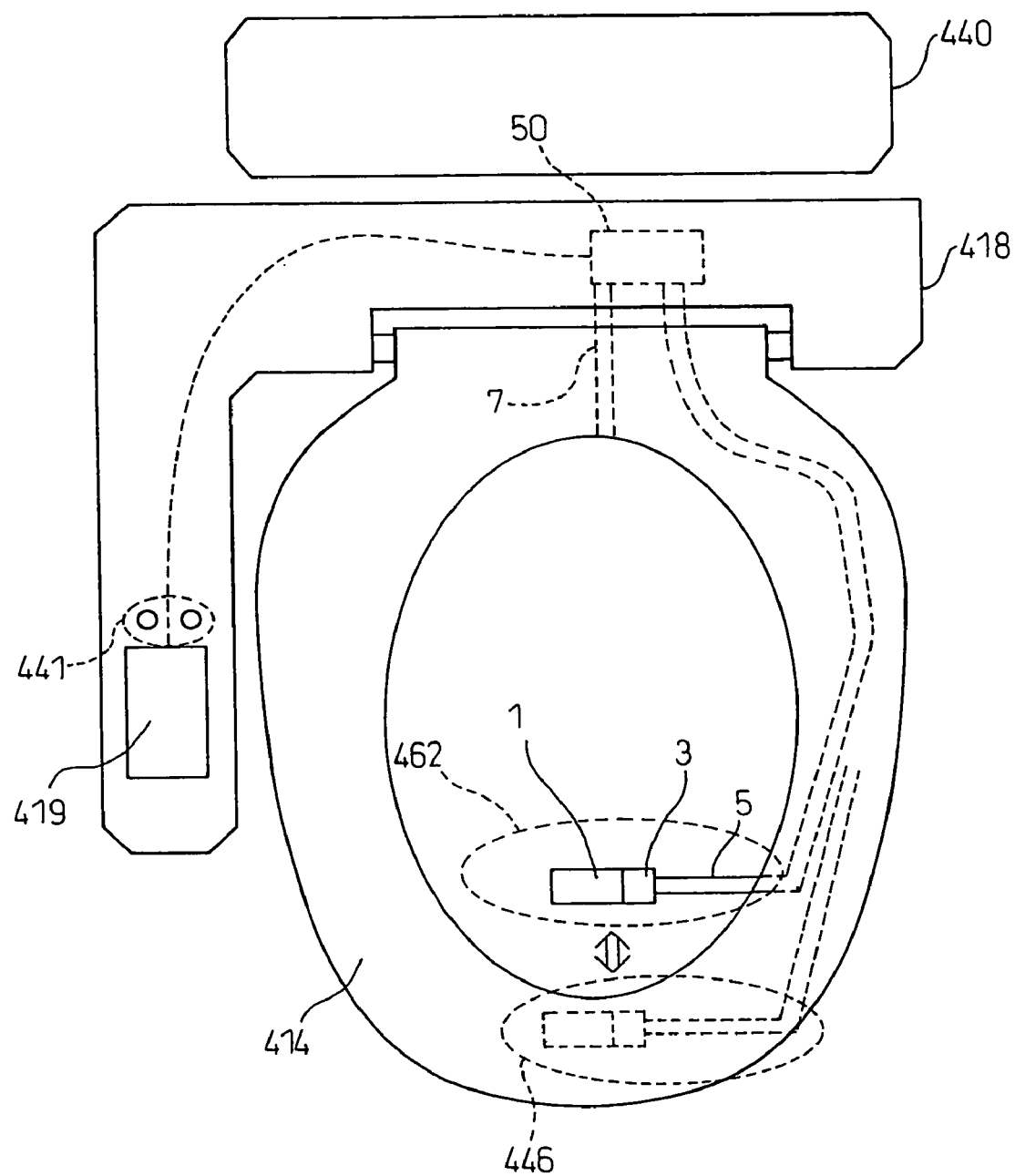
FIG. 23 is a diagram showing an example in which the optical measurement apparatus is built into a toilet seat.

FIG. 23 is a diagram showing an example in which the optical measurement apparatus is built into a toilet seat.

As shown in FIG. 23, the toilet comprises a toilet main unit 418, a toilet seat 418, a water tank 440, etc. In the example of FIG. 23, the optical measurement apparatus shown in FIG. 1 is built into the toilet seat 414 (the electromagnetic valve 2 is omitted).

The urine collection container 1 and the ion-exchange resin section 3 are normally located in a holding position 46 on the reverse side of the toilet seat 14, but when the measurement start button 441 is pressed, they are moved to a urine collection position 462 by a moving mechanism not shown. The urine collected in the urine collection container 1 is conveyed through the tube 5 and fed to the optical system 50. When the measurement is completed, the urine is discharged through the tube 7 into the toilet bowl. The measurement result is displayed on the display section 419.

Figure 24:
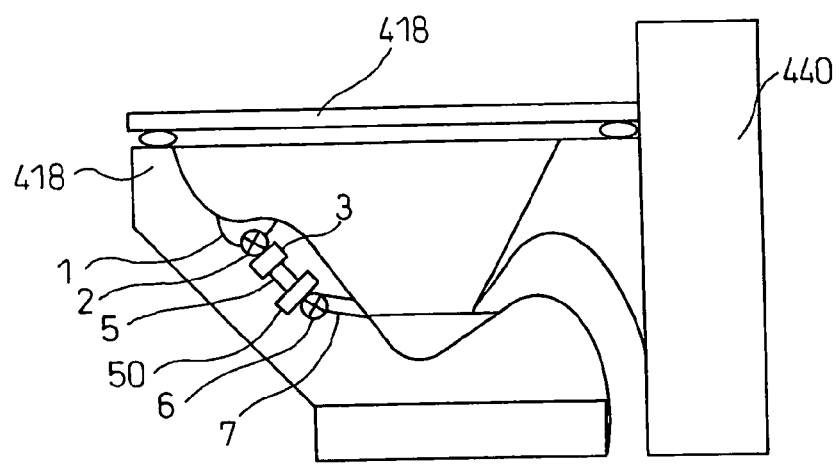
FIG. 24 is a diagram showing an example in which the optical measurement apparatus is built into a toilet bowl.

FIG. 24 is a diagram showing an example in which the optical measurement apparatus is built into a toilet bowl.

As shown in FIG. 24, the toilet comprises a toilet main unit 418, a toilet seat 418, a water tank 440, etc. In the example of FIG. 24, the optical measurement apparatus shown in FIG. 1 is built into the toilet main unit 418.

The urine collected in the urine collection container 1 installed in the toilet main unit 418 is passed through the electromagnetic valve 2, ion-exchange resin section 3, and tube 5 and fed to the optical system 50. When the measurement is completed, the electromagnetic valve 6 is opened and the urine is discharged through the tube 7 into the toilet bowl.

FIGS. 23 and 24 have each shown an example in which the optical measurement apparatus shown in FIG. 1 is built into the toilet seat or the toilet bowl, but it will be appreciated that the apparatus of other embodiments can also be built into the toilet seat or the toilet bowl.

What is claimed is:

1. An optical measurement apparatus comprising:
   an ion-exchange resin;
   a synthetic absorbent;
   an optical measurement section for measuring the concentration of an optically active substance in a sample based on optical characteristics of said optically active substance after said sample is passed through said ion-exchange resin and said synthetic absorbent;
   a control section for continuously monitoring a measurement result from said optical measurement section; and
   a regenerating section for regenerating said ion-exchange resin with a regenerant, wherein
   said control section makes a determination, based on the monitoring of said measurement result, as to whether ion-exchange ability of said ion-exchange resin has become saturated or not, and
   said control section conducts a regeneration by said regenerating section when said control section determines that said ion-exchange resin has become saturated.

2. The optical measurement apparatus according to claim 1, wherein said regenerating section regenerates said ion-exchange resin with alkaline ionized water.

3. The optical measurement apparatus according to claim 2, wherein said regenerating section includes an alkaline ionized water producing section for producing said alkaline ionized water from tap water.

4. The optical measurement apparatus according to claim 1, wherein said regenerating section regenerates said ion-exchange resin with acid water.

5. The optical measurement apparatus according to claim 4, wherein said regenerating section includes an acid water producing section for producing said acid water from tap water.

6. The optical measurement apparatus according to claim 1, wherein said regenerating section also cleans said ion-exchange resin with tap water.

7. The optical measurement apparatus according to claim 1, wherein said ion-exchange resin is replaceably mounted.

8. The optical measurement apparatus according to claim 1, wherein said ion-exchange resin is a weak base ion-exchange resin.

9. The optical measurement apparatus according to claim 1, wherein said ion-exchange resin is filled into a column having a transparent window.

10. The optical measurement apparatus according to claim 9, further comprising a detecting section for detecting the color of said ion-exchange resin.

11. The optical measurement apparatus according to claim 1, wherein said control section computes the concentration of said optically active substance by using the measurement result obtained when said measurement result has settled to a steady-state value.

12. The optical measurement apparatus according to claim 1, wherein said optically active substance is urine sugar.

13. The optical measurement apparatus according to claim 1, wherein said ion-exchange resin is an anion-exchange resin, a mixed-bed ion-exchange resin, or a cation-exchange resin.

14. The optical measurement apparatus according to claim 1, wherein said control section makes a determination, based on the monitoring of said measurement result, as to the degree to which said ion-exchange resin has been regenerated by said regenerant.

15. The optical measurement apparatus according to claim 1, wherein said control section controls the amount of said regenerant.

16. The optical measurement apparatus according to claim 1, wherein said optical measurement apparatus is installed in a toilet seat or a toilet bowl.

* * * * *